US006726651B1

(12) United States Patent
Robinson et al.

(10) Patent No.: US 6,726,651 B1
(45) Date of Patent: Apr. 27, 2004

(54) METHOD AND APPARATUS FOR DIFFERENTIALLY PERFUSING A PATIENT DURING CARDIOPULMONARY BYPASS

(75) Inventors: Janine Robinson, Half Moon Bay, CA (US); Wilfred J. Samson, Saratoga, CA (US); John A. Macoviak, La Jolla, CA (US); Lisa M. Young, Campbell, CA (US); Brady Esch, San Jose, CA (US); Mike Lee, San Francisco, CA (US); Eric Olsen, Los Gatos, CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/368,450

(22) Filed: Aug. 4, 1999

(51) Int. Cl.$^7$ .................. A61M 29/00; A61M 37/00
(52) U.S. Cl. .................. 604/101.01; 604/4.01; 604/102.01
(58) Field of Search ................. 604/4, 101.01, 604/101.03–101.05, 102.01, 102.03, 103.1, 164.01, 164.09, 164.1, 96.01, 264, 265, 524, 533–535; 606/192, 194

(56) References Cited

U.S. PATENT DOCUMENTS

| | | | |
|---|---|---|---|
| 3,996,938 A | 12/1976 | Clark, III | 128/348 |
| 4,173,981 A | 11/1979 | Mortensen | 128/348 |
| 4,494,531 A | 1/1985 | Gianturco | 128/1 R |

(List continued on next page.)

FOREIGN PATENT DOCUMENTS

| | | | |
|---|---|---|---|
| EP | 0 218 275 A | 4/1987 | |
| WO | WO 97/17100 | 5/1997 | A61M/29/00 |
| WO | WO 97/42879 | 11/1997 | A61B/17/00 |
| WO | WO 98/02084 | 1/1998 | |
| WO | WO 98/24377 | 6/1998 | A61B/17/22 |
| WO | WO 99/04848 | 2/1999 | A61M/29/00 |

OTHER PUBLICATIONS

Barbut et al., "Determination or Size of Aortic Emboli and Embolic Load During Coronary Artery Bypass Grafting," *Ann Thorac Surg*; 63:1262–7 (1997).

Barbut et al., "Aortic Atheromatosis and Risks of Cerebral Embolization," *J Card & Vasc Anesth*; Vol 10, No 1,; pp 24–30 (1996).

Barbut et al., "Aortic Atheroma is Related to Outcome but not Numbers of Emboli During Coronary Bypass," *Ann Thorac Surg*; 64:454–9 (1997).

Roach et al., "Adverse Cerebral Outcomes After Coronary Artery Bypass Surgery," *N Engl J Med*, Vol 335, No 25; pp. 1857–1863 (1996).

Aberg, "Signs of Brain Cell Injury During Open Heart Operations: Past and Present," *Ann Thorac Surg*; 59:1312–5 (1995).

Murkin, "The Role of CPB Management in Neurobehavioral Outcomes After Cardiac Surgery," *Ann Thorac Surg*; 59:1308–11 (1995).

Mills, "Risk Factors for Cerebral Injury and Cardiac Surgery," *Ann Thorac Surg* 1995, 59:1296–9.

Moody et al., "Brain Microemboli Associated with Cardiopulmonary Bypass: A Histologic and Magnetic Resonance Imaging Study," *Ann Thorac Surg*; 59:1304–7 (1995).

(List continued on next page.)

*Primary Examiner*—Michael J. Hayes
(74) *Attorney, Agent, or Firm*—Fulwider Patton Lee & Utecht, LLP

(57) ABSTRACT

The present invention provides methods, systems and devices for performing cardipulmonary bypass (CPB), cardioplegic arrest, suction of fluid from the aorta to remove embolic or other fluid from the general circulation and the selective segmentation of the arterial system to perform differential perfusion eliminating hypoperfusion. An aortic catheter having an arch lumen which extends at least in part along the length of the catheter shaft has a proximal opening coupled to a CPB machine and a distal arch opening. A corporeal lumen extends at least in part along the length of the catheter shaft and has a proximal opening coupled to a CPB machine and a distal corporeal opening. A suction lumen extends at least in part along the length of the catheter shaft and has a proximal suction opening coupled to a suction source and a distal suction opening residing in the aortic lumen of a patient.

22 Claims, 19 Drawing Sheets

U.S. PATENT DOCUMENTS

| | | | |
|---|---|---|---|
| 4,527,549 A | | 7/1985 | Gabbay .......................... 128/1 |
| 4,573,966 A | * | 3/1986 | Weikl et al. ................... 604/53 |
| 4,650,466 A | | 3/1987 | Luther .......................... 604/95 |
| 4,661,094 A | | 4/1987 | Simpson ...................... 604/53 |
| 4,723,549 A | | 2/1988 | Wholey et al. ............. 128/344 |
| 4,741,328 A | | 5/1988 | Gabbay .......................... 128/1 |
| 4,793,348 A | | 12/1988 | Palmaz ....................... 128/325 |
| 4,817,600 A | | 4/1989 | Herms et al. ............... 128/303 |
| 4,873,978 A | | 10/1989 | Ginsburg .................... 128/345 |
| 4,911,163 A | * | 3/1990 | Fina ............................ 606/127 |
| 4,968,306 A | | 11/1990 | Huss et al. ................. 604/264 |
| 4,969,891 A | | 11/1990 | Gewertz ..................... 606/200 |
| 5,059,205 A | | 10/1991 | El-Nounou et al. ........ 606/200 |
| 5,108,418 A | | 4/1992 | Lefebvre .................... 606/200 |
| 5,108,419 A | | 4/1992 | Reger et al. ................ 606/200 |
| 5,152,777 A | | 10/1992 | Goldberg et al. ........... 606/200 |
| 5,216,032 A | | 6/1993 | Manning .................... 514/718 |
| 5,308,320 A | | 5/1994 | Safar et al. ..................... 604/4 |
| 5,312,344 A | | 5/1994 | Grinfeld ...................... 604/101 |
| 5,324,304 A | | 6/1994 | Rasmussen ................. 606/200 |
| 5,330,433 A | | 7/1994 | Fonger et al. ............... 604/164 |
| 5,334,142 A | | 8/1994 | Paradis ......................... 604/53 |
| 5,354,288 A | | 10/1994 | Cosgrove et al. ........... 604/264 |
| 5,375,612 A | | 12/1994 | Cottenceau et al. ........ 128/899 |
| 5,383,854 A | | 1/1995 | Safar et al. ................... 604/98 |
| 5,413,558 A | | 5/1995 | Paradis ....................... 604/101 |
| 5,415,630 A | | 5/1995 | Gory et al. .................... 604/53 |
| 5,425,724 A | | 6/1995 | Akins .......................... 604/284 |
| 5,433,700 A | | 7/1995 | Peters ............................. 604/4 |
| 5,437,633 A | | 8/1995 | Manning ....................... 604/53 |
| 5,451,207 A | | 9/1995 | Yock ............................. 604/53 |
| 5,458,574 A | | 10/1995 | Machold et al. ............ 604/101 |
| 5,478,309 A | | 12/1995 | Sweezer et al. ................ 604/4 |
| 5,496,277 A | | 3/1996 | Termin et al. ............... 604/104 |
| 5,522,834 A | | 6/1996 | Fonger et al. ............... 606/194 |
| 5,531,776 A | | 7/1996 | Ward et al. .................. 607/105 |
| 5,549,626 A | | 8/1996 | Miller et al. ................ 606/200 |
| 5,584,803 A | | 12/1996 | Stevens et al. ................ 604/4 |
| 5,599,329 A | | 2/1997 | Gabbay ....................... 604/284 |
| 5,616,137 A | | 4/1997 | Lindsay ...................... 604/264 |
| 5,662,671 A | | 9/1997 | Barbut et al. ............... 606/170 |
| 5,678,570 A | | 10/1997 | Manning .................... 128/897 |
| 5,685,865 A | | 11/1997 | Cosgrove et al. ........... 604/239 |
| 5,695,457 A | | 12/1997 | St. Goar et al. ................ 604/4 |
| 5,697,905 A | | 12/1997 | d'Ambrosio ................. 604/96 |
| 5,702,368 A | | 12/1997 | Stevens et al. ............. 604/171 |
| 5,716,318 A | | 2/1998 | Manning ...................... 600/16 |
| 5,725,496 A | | 3/1998 | Peters .......................... 604/49 |
| 5,738,649 A | | 4/1998 | Macoviak .................... 604/43 |
| 5,738,652 A | | 4/1998 | Boyd et al. ................... 604/96 |
| 5,755,687 A | | 5/1998 | Donlon et al. ................ 604/53 |
| 5,755,784 A | | 5/1998 | Jarvik ........................... 623/3 |
| 5,759,170 A | | 6/1998 | Peters ............................ 604/4 |
| 5,766,151 A | | 6/1998 | Valley et al. ................. 604/96 |
| 5,769,812 A | | 6/1998 | Stevens et al. ................ 604/4 |
| 5,769,816 A | | 6/1998 | Barbut et al. ................ 604/96 |
| 5,769,828 A | | 6/1998 | Jonkman .................... 604/280 |
| 5,776,190 A | | 7/1998 | Jarvik ........................... 623/3 |
| 5,792,094 A | | 8/1998 | Stevens et al. ................ 604/4 |
| 5,795,325 A | | 8/1998 | Valley et al. ................. 604/53 |
| 5,800,375 A | | 9/1998 | Sweezer et al. ................ 604/4 |
| 5,810,757 A | | 9/1998 | Sweezer et al. ................ 604/4 |
| 5,814,016 A | | 9/1998 | Valley et al. ................. 604/96 |
| 5,820,593 A | | 10/1998 | Safar et al. .................... 604/96 |
| 5,827,237 A | | 10/1998 | Macoviak et al. .......... 604/246 |
| 5,833,671 A | | 11/1998 | Macoviak et al. .......... 604/247 |
| 5,846,260 A | | 12/1998 | Maahs ........................ 606/200 |
| 5,868,702 A | * | 2/1999 | Stevens et al. .......... 604/96.01 |
| 5,906,588 A | | 5/1999 | Safar et al. .................... 604/64 |
| 6,083,198 A | * | 7/2000 | Afzal ..................... 604/101.01 |
| 6,090,096 A | * | 7/2000 | St. Goar et al. ............ 604/509 |
| 6,283,127 B1 | * | 9/2001 | Sterman et al. ............. 128/898 |

OTHER PUBLICATIONS

Murkin et al., "Statement of Consensus on Assessment of Neurobehavioral Outcomes After Cardiac Surgery," *Ann Thorac Surg*: 59:1289–95 (1995).

Sherman et al., "Heart–Brain Interactions: Neurocardiology Comes of Age," *Mayo Clin Proc*; 62:1158–1160 (1987).

van der Linden, "Cerebral Hemodynamics After Low–Flow Versus No–Flow Procedures," *Ann Thorac Surg*; 59:1321–5 (1995).

Newman et al., "Predictors of Cognitive Decline After Cardiac Operation," *Ann Thorac Surg*; 59:1326–30 (1995).

Venn et al., "Cardiopulmonary Bypass: Perioperative Cerebral Blood Flow and Postoperative Cognitive Deficit," *Ann Thorac Surg*; 59:1331–5 (1995).

Blauth, "Macroemboli and Microemboli During Cardiopulmonary Bypass," *Ann Thorac Surg*; 59:1300–3 (1995).

Sotaniemi, "Long–Term Neurologic Outcome After Cardiac Operation," *Ann Thorac Surg*; 59:1336–9 (1995).

Technical Specification Datascope Corp Percluder® Aortic Occluding Balloon. © 1987 Datascope Corp.

Rogers AT, Neurological Effects of Cardiopulmonary Bypass; Cardiopulmonary Bypass Principles and Practice; Gravlee GP, 21:542.

Erath et al., "Balloon Catheter Occulsion of the Ascending Aorta," *Ann Thorac Surg*; 35:560–1 (1983).

Cosgrove DM, "Management of the Calcified Aorta: and Alternative Method of Occlusion," *Ann Thor Surg*; 36:718–719 (1983).

Baxter Research Medical, RMI Dispersion™ Aortic Cannula, Advertisement (1998).

3M™ Sarns™ Soft Flow Aortic Arch Cannula pp. 1–4, Advertisement (1994).

Research Medical™ Instructions for Use, RMI Aortic Arch Cannula Rev 5 (1994).

Braekken et al. "Cerebral Microembolic Signals During Cardiopulmonary Bypass Surgery. Frequency, Time of Occurrence, and Association with Patient and Surgical Characteristics." *Stroke*; 1988–92. (1997).

Okita et al. "Utilization of Triple Lumen Balloon Catheter for Occulsion of The Ascending Aorta During Distal Aortic Arch Surgery With Hypothermic Retrograde Cerebral Circulation Technique Through Left Thorocotomy." *J Card Surg*; 10:699–702 (1995).

Rubenstein et al. "Percutaneous Aortic Balloon Occlusion." *Surg Gynecol Obstet*; 164:561–563 (1987).

Muehrcke et al. "Flow Characteristics of Aortic Cannulae." *J Card Surg*; 10:514–519 (1995).

Robicsek, "Administration of Hypothermic Cardioplegia in the Presence of Aortic Regurgitation." *Ann Thorac Surg*. Feb;39(2):192–3 (1985).

Hirose, "Use of the Balloon Catheter for Distal Occlusion of the Aorta in Prosthetic Replacement of Aortic Arch Aneurysms," *Ann Thorac Surg*. 1985 Jun;39(6):538–40.

Schwartz AE, Selective cerebral hypothermia by means of transfemoral internal carotid artery catheterization. *Radiology*, 1996 Nov;201(2):571–2.

Schwartz AE, "Isolated cerebral hypothermia by single carotid artery perfusion of extracorporeally cooled blood in baboons." *Neurosurgery*, 1996 Sep;39(3):577–81; discussion 581–2.

* cited by examiner

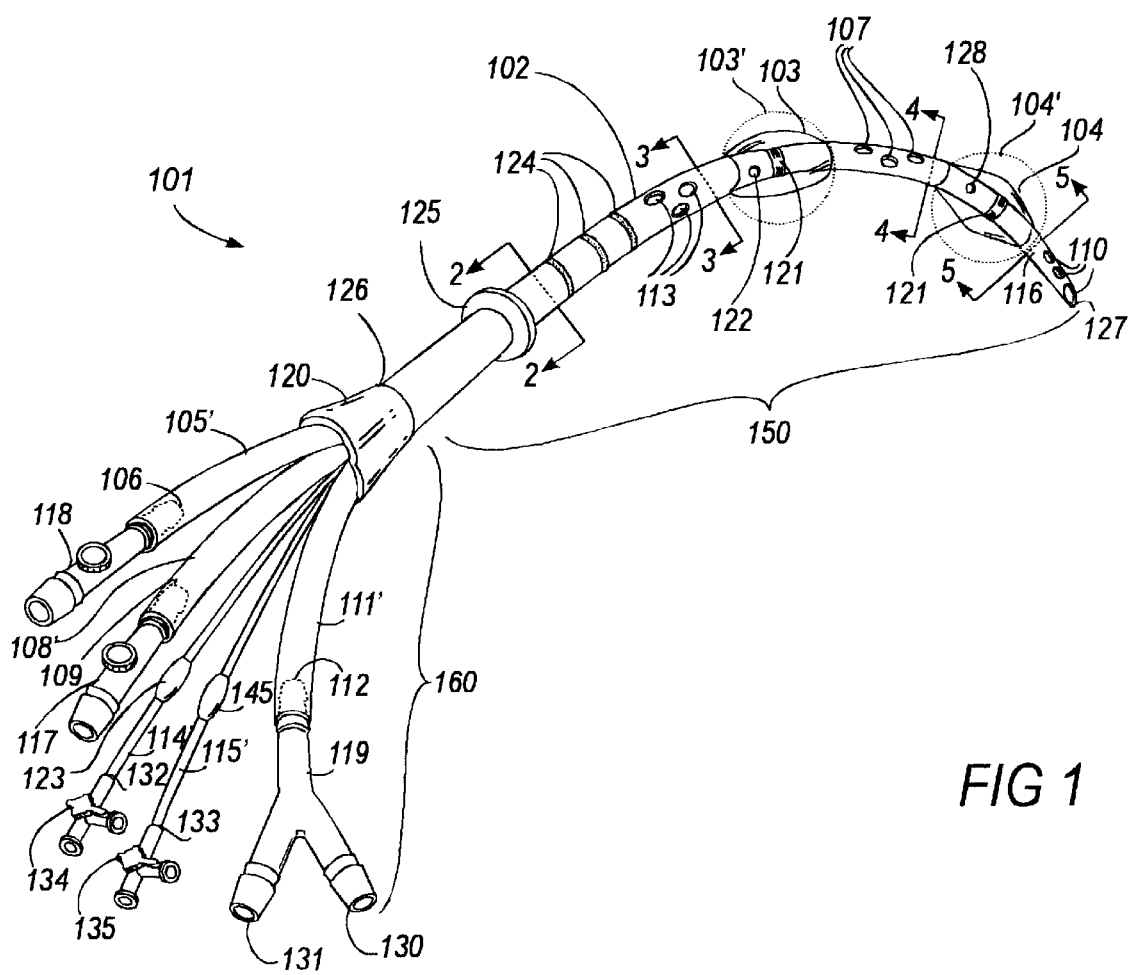
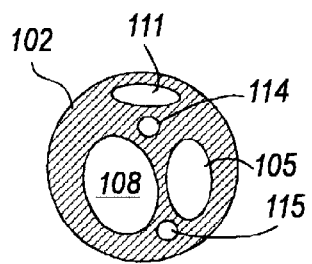
FIG 2
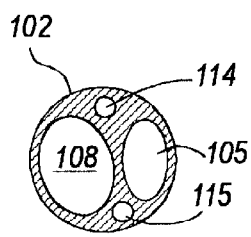
FIG 3
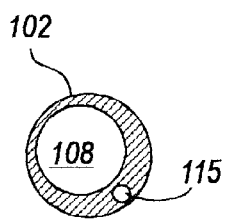
FIG 4
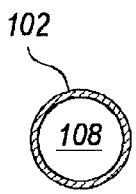
FIG 5
FIG 1

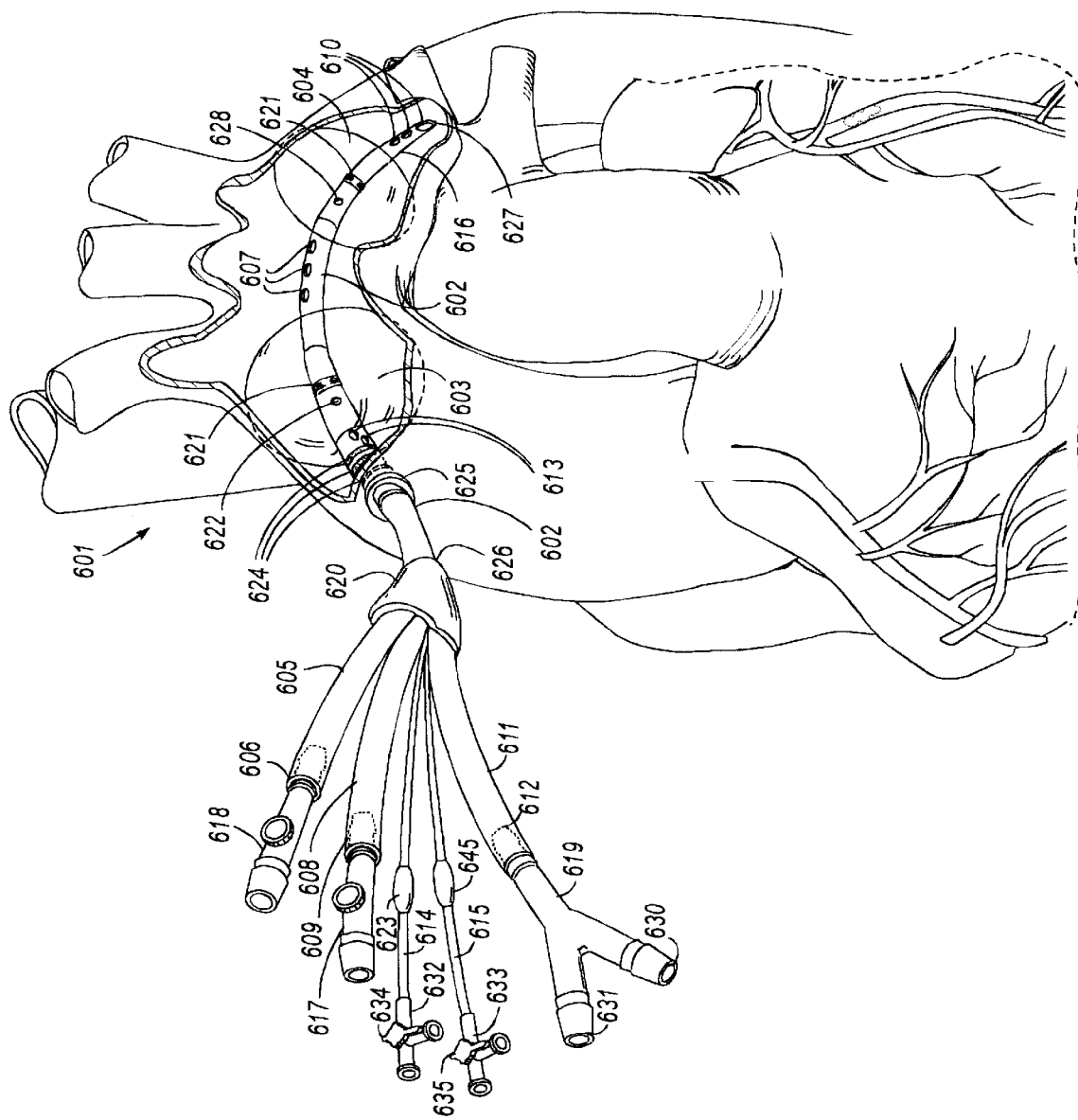

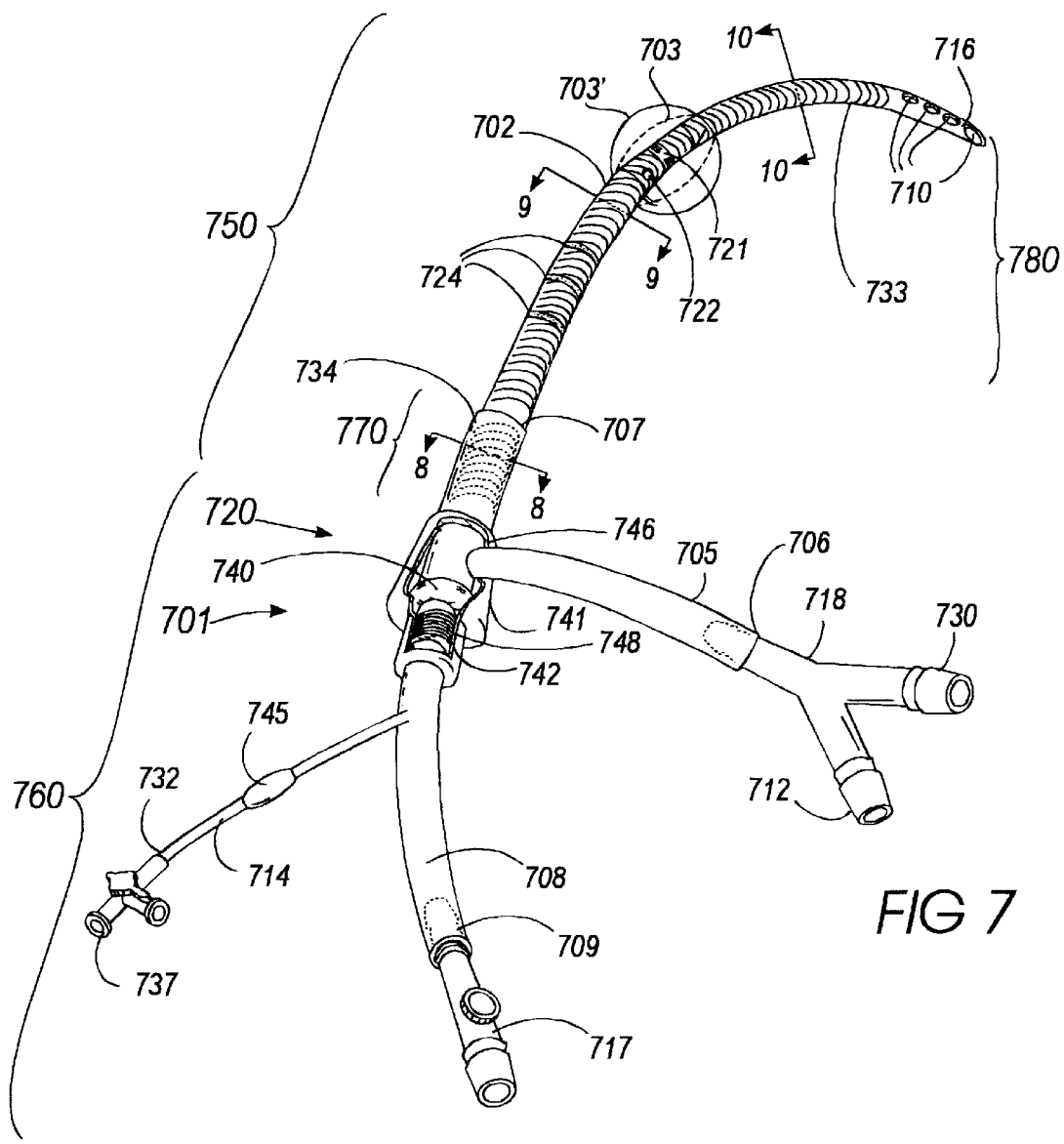
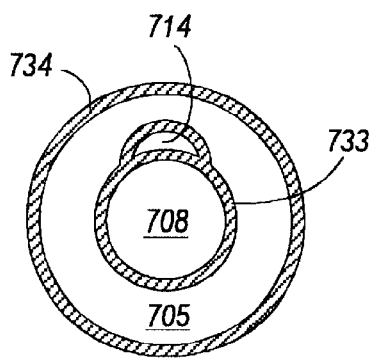
FIG 8
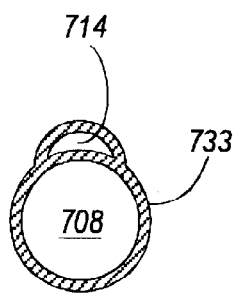
FIG 9
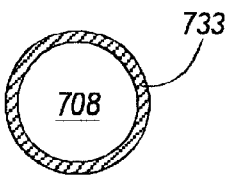
FIG 10

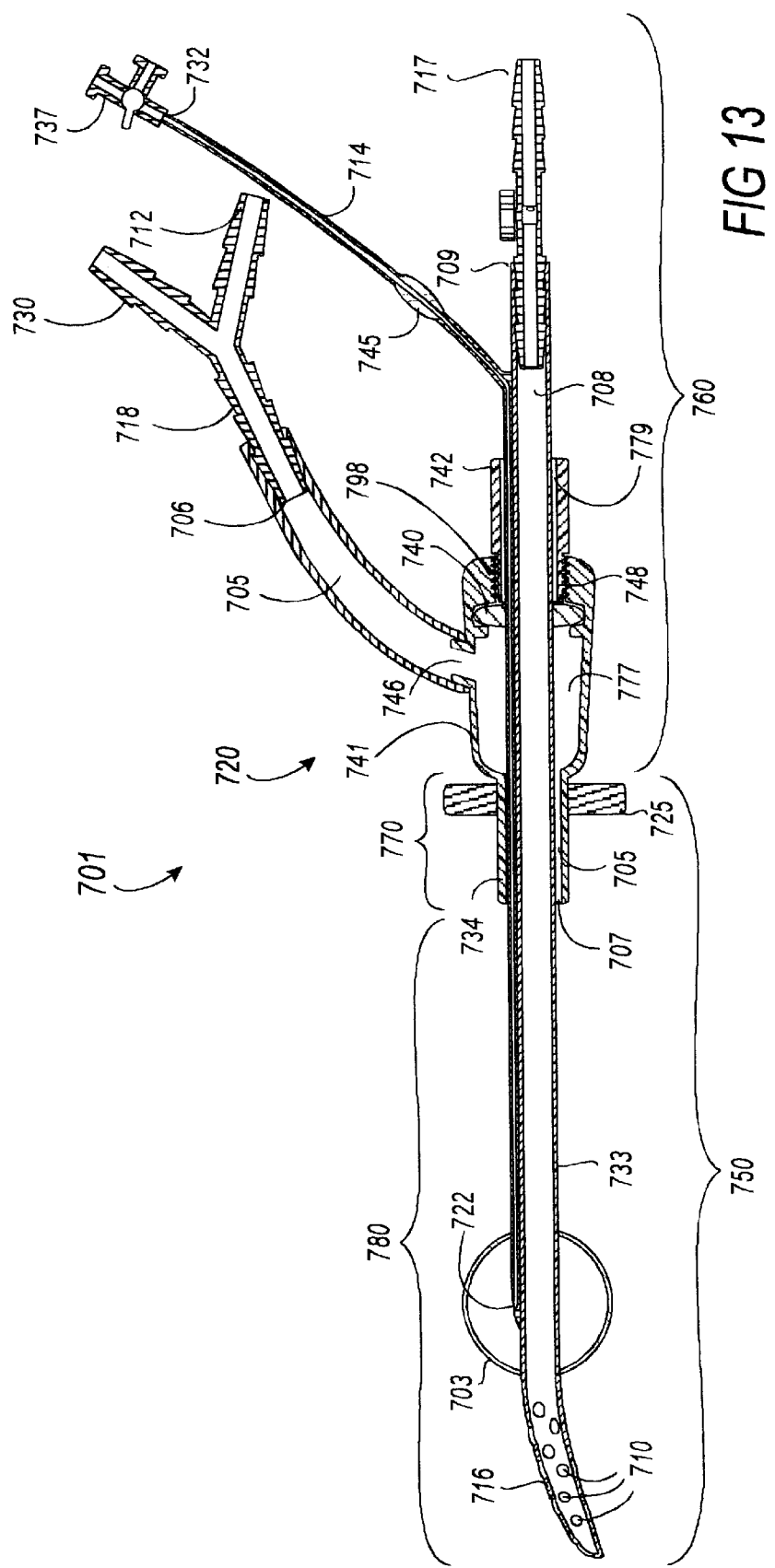

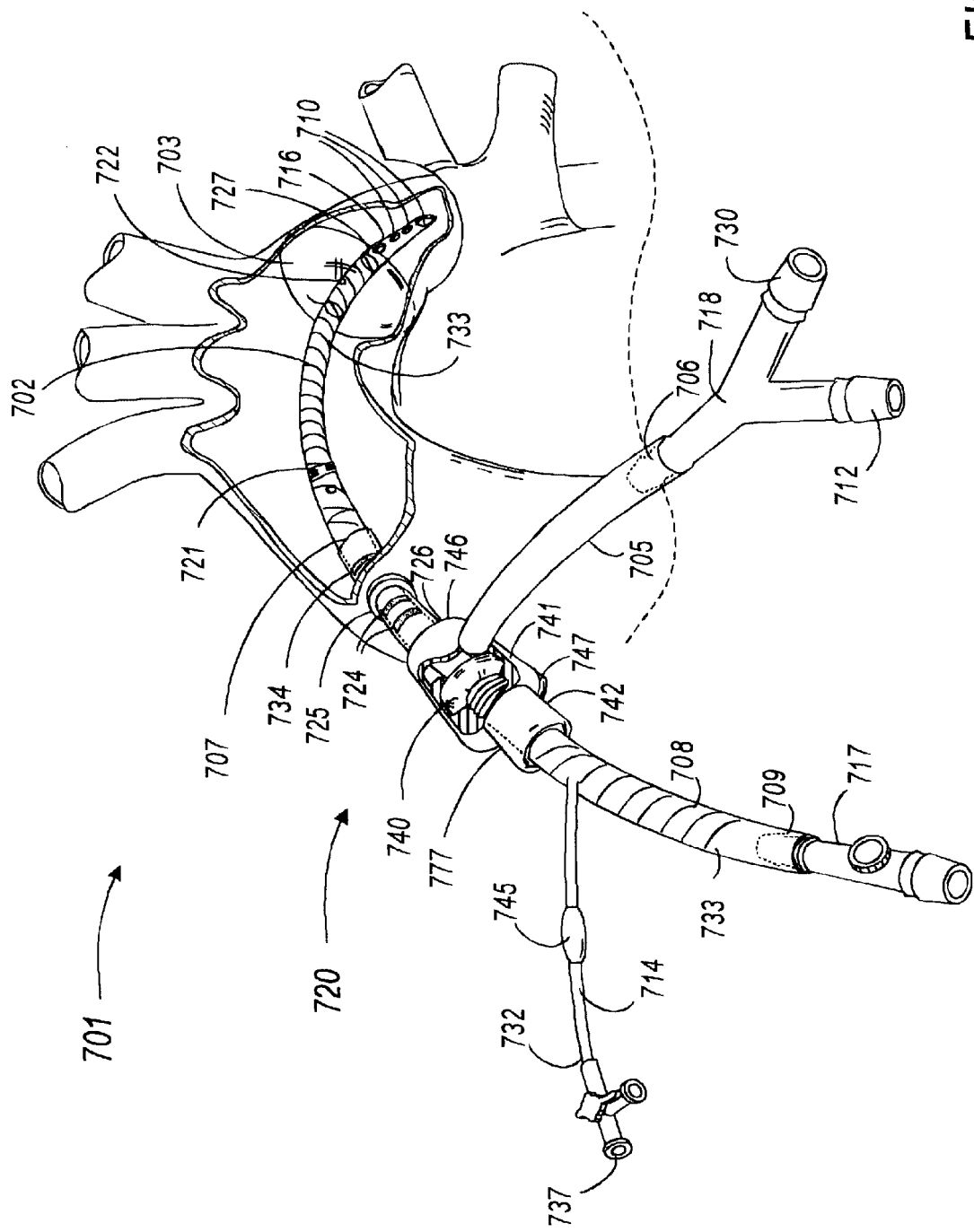

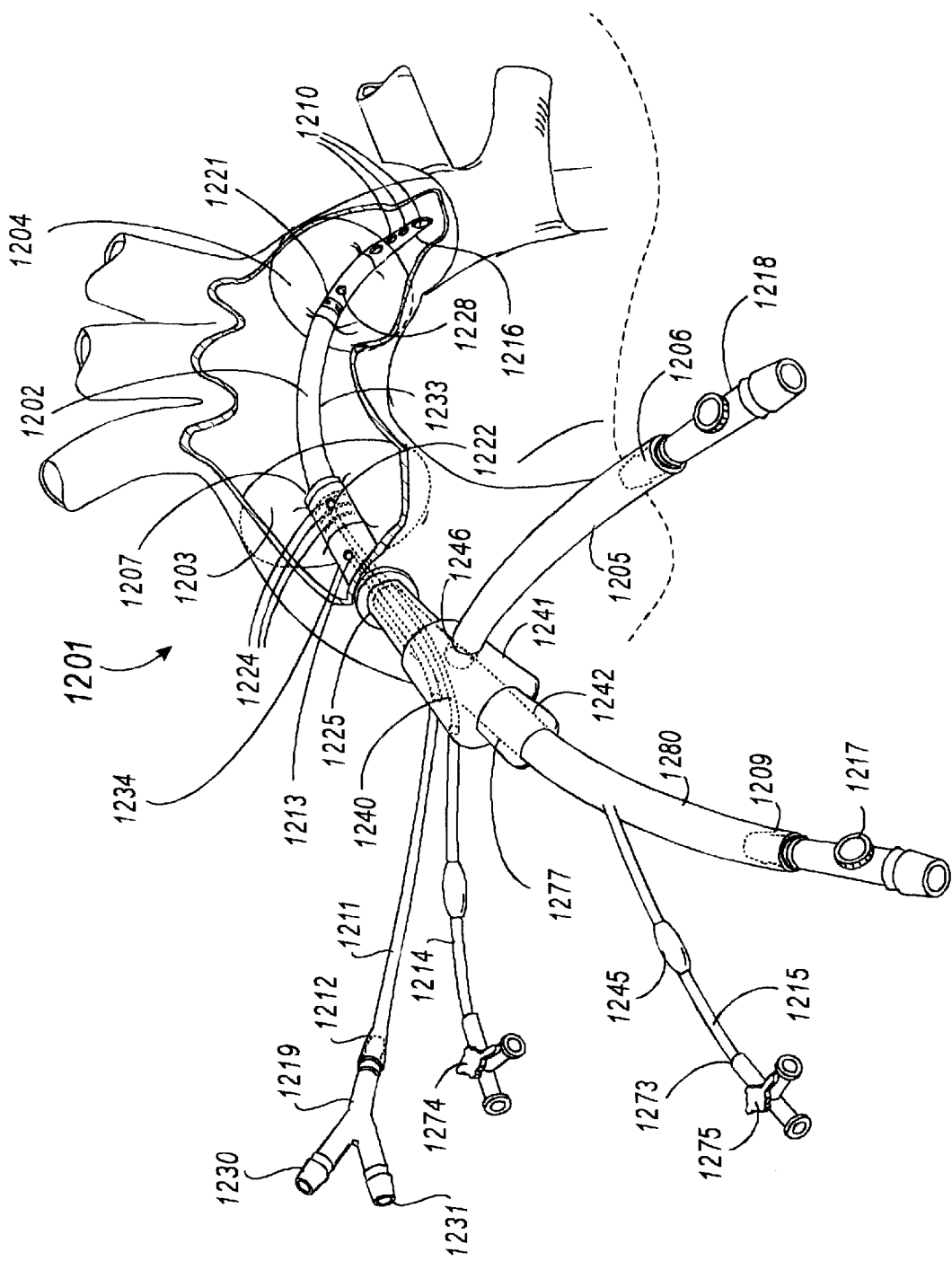

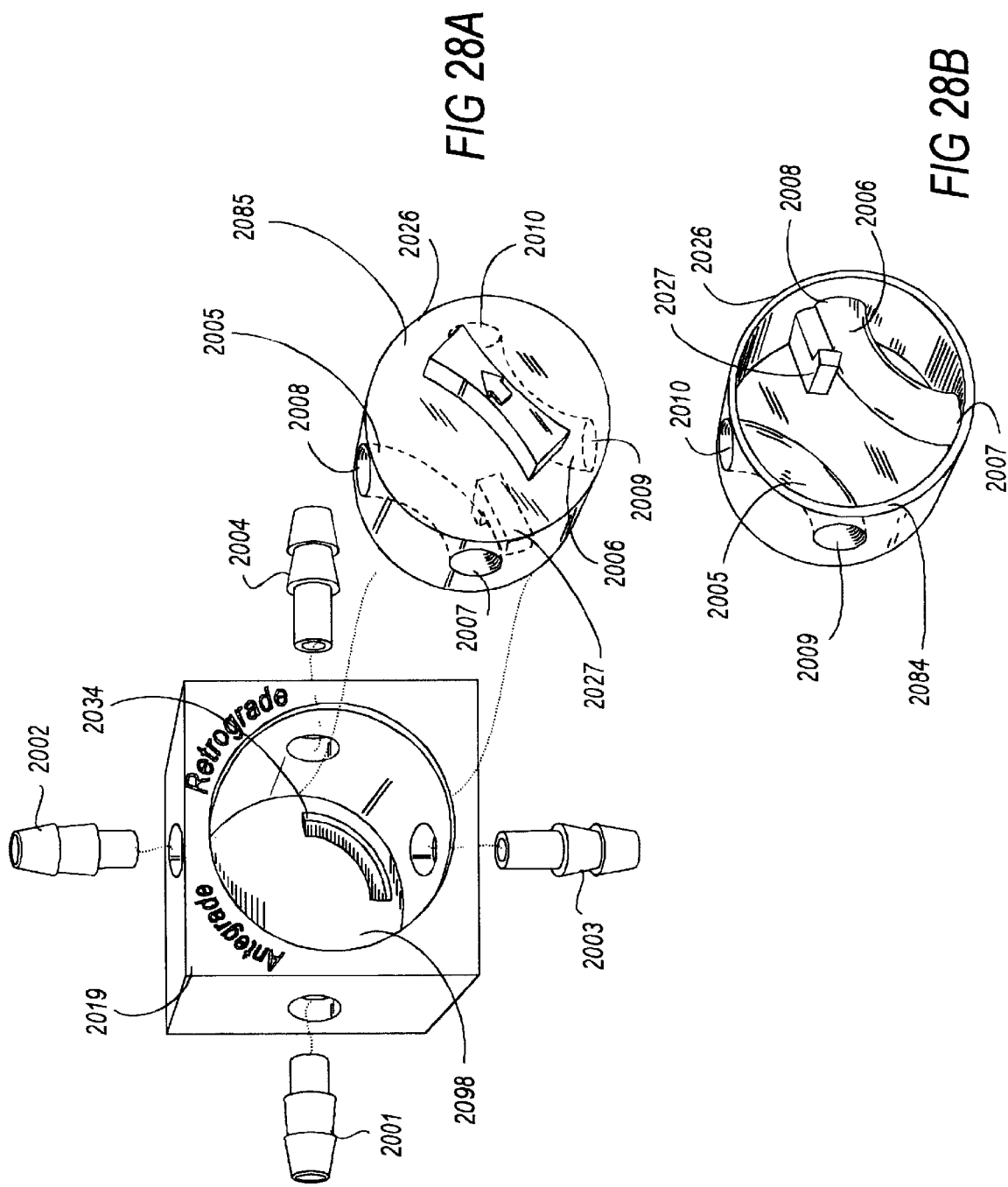

METHOD AND APPARATUS FOR DIFFERENTIALLY PERFUSING A PATIENT DURING CARDIOPULMONARY BYPASS

FIELD OF THE INVENTION

The present invention relates generally to medical devices to be used during cardiovascular, pulmonary, and neurologic procedures where a cardiopulmonary bypass machine is used. More specifically, the present invention incorporates a cardiopulmonary bypass machine and an aortic catheter to provide neurological protection through differential perfusion and suction.

BACKGROUND OF THE INVENTION

In general, there has been a steady decline in the amount of cardiac morbidity and operative mortality directly associated with cardiopulmonary bypass (CPB) in recent years. Enhanced myocardial protection, more complete coronary revascularization, improved operating technique resulting in enhanced graft patency rates, and better general patient support such as improved cardiac anesthesia and intensive care practices have been cited as some of the primary reasons for better surgical outcomes. Blumenthal J A, et al. "Methodological Issues in the Assessment of Neuropsychologic Function After Cardiac Surgery," *Ann Thorac Surg;* 59:1345–50 (1995). However, despite the overall decrease in morbidity and mortality, the incidence of neurologic deficit, in the form of, fatal cerebral injury, stroke, retinal microvascular pathology, impaired level of consciousness, seizures, spinal cord injury, peripheral nerve injury and neuropsychologic deficit has increased.

The occurrence of neurologic deficit, after a cardiac procedure, depends upon a number of factors including: the type of operation, the age of the patient population, the prospective versus retrospective nature of the studies, and the sensitivity of the tests performed. Mills, "Risk Factors for Cerebral Injury and Cardiac Surgery," *Ann Thorac Surg* 1995, 59:1296–1299. Evidence has suggested that the incidence of stroke, the most dramatic form of neurologic deficit approaches 9% in patients greater than 75 years of age. In addition, severe aortic atheroma is a disease strongly linked to stroke and rises sharply with an increase in age. These correlative factors combined with a subsequent change in population demographics have allowed more high-risk patients, most notably the elderly, to be treated by cardiac surgery and unfortunately, with the attendant risk of neurologic deficit. Nevertheless, even though there is a greater risk of neurologic deficit with an increase in age, the inherent complications of cardiac surgery place all age groups, not just the elderly, at risk.

Neuropsychological testing, a means to quantify subtle cognitive changes in patients due to cerebral damage, has shown that as many as two-thirds of patients undergoing CPB demonstrate some type of neuropsychological deficit postoperatively. The affects of neuropsychologic deficit on any single patient are wide ranging and depend upon the patient's activity level and intellectual pursuits before surgery, however, common disabilities incurred by patients are impaired memory, concentration and hand eye coordination, with a predictably negative impact on life. Rogers A T, Newman S P, Stump D A, Prough D S: Neurologic Effects of Cardiopulmonary Bypass, in Gravlee G P, Davis R F Utley J R: *Cardiopulmonary Bypass Principles and Practice.* Baltimore: Williams and Wilkins, 1993, pp. 542–576.

In patients undergoing CPB surgery, substantial amounts of clinical data have shown that the primary etiological mechanisms contributing to neurologic and neuropsychologic deficit are cerebral embolization and hypoperfusion. Cerebral embolic infarction occurs when emboli, such as: platelet aggregation, aggregates of fibrin, clusters of microbubbles, boluses of air, and atherosclerotic plaques, are released into the general blood circulation and lodge in the brain. Hypoperfusion, a second theorized culprit, can potentially create cerebral ischemia, which may result in permanent cerebral infarction due to a lack of oxygenated blood flow to the brain.

Transcranial Doppler Ultrasonography (TCD) and Transcarotid Doppler Echocardiography have been used to measure and detect embolic signals, thereby quantifying when in surgical procedures embolic events are most likely to occur. Results have shown that atheromatous plaque can be released into the general blood circulation when there is cannulation of the aorta, manipulation of the heart and ascending aorta, and application or release of the cross-clamp or side biting clamp to the aorta. Furthermore, boluses of air or "surgical air" can enter the general blood circulation when there is cannulation of the heart or aorta and removal of the cross clamp, at the site of venous cannulation and when a surgical intervention requires the opening of the cardiac chambers. In addition, some believe that the extracorporeal circuit can be an ongoing source of potential embolic events. For instance, blood born emboli, such as platelet aggregation and fibrin can occur when anticoagulated blood contacts a foreign surface throughout the extracorporeal circuit and microbubbles may be formed within bubble oxygenators and membrane oxygenators in the extracorporeal circuit. Nevertheless, of all the types of emboli and the sources thereof, it is still unclear as to what type of embolic insult is of greatest detriment to the patient: total embolic volume, constitution of emboli, collateral arterial blood supply of the territory affected or the quality of preexisting parenchymal brain function. Barbut et al., "Aortic Atheromatosis and Risks of Cerebral Embolization," *J Card & Vasc Anesth;* Vol 10, No 1: pp 24–30 (1996).

As is evident from the foregoing discussion, emboli can be released in a number of different ways and in a number of different forms. In addition, an increase in perfusion to resolve the problem of hypoperfusion can potentially expose the brain to more embolic debris since more blood flow is going to the cerebral circulation. Alternatively, a reduction in perfusion lowers the overall flow, volume and cycles of blood to the brain, which has the resultant effect of providing less opportunity for emboli to be introduced into the cerebral blood circulation, but may increase the deleterious effects of hypoperfusion.

Therefore, what has been needed and heretofore unavailable is a method and device for reducing cerebral embolism and eliminating hypoperfusion by assuring that adequate blood flow is being supplied to the brain. Substantial strides have been made addressing either embolic insult or hypoperfusion, but not both in the same device. The present invention solves both of these immediate problems, as well as others.

For example, various strategies have been proposed to mitigate the danger of embolic events during CPB surgery. The use of transesophageal echocardiography (TEE) has been used to assess the extent and severity of atherosclerotic plaque, in patients being diagnosed as having aortic atheroma, in order to optimize cannulation sites and minimize the release of plaque into the general blood circulation arising from aortic cannulation. Arterial line filters, bubble traps, air bubble detectors and the wide spread use of membrane oxygenators have reduced the amount of gaseous emboli released into the general blood circulation. Furthermore, rigorous deairing techniques have been shown to help remove "surgical air", and a general awareness that the manipulation of the heart and aorta can potentially create an embolic event has substantially changed surgical techniques to try and limit these maneuvers. However, none of these techniques address hypoperfusion.

Even more recently, patent literature has disclosed devices and methods for reducing the amount of emboli during surgical interventions. Advances have been made which incorporate filters to trap emboli that may be released during CPB surgery. Patents describing these features include: U.S. Pat. Nos. 5,662,671, 5,769,816 and 5,846,260; WO 97/17100, WO 97/42879, WO 98/02084 and commonly owned, copending patent application Ser. No. 09/158,405 filed on Sep. 22, 1998, by Macoviak et al. In addition, WO 98/24377 describes a carotid filter for accomplishing the same general result.

Other related technologies that reduce cerebral insult caused by emboli are intra-aortic shunts and deflectors, which are described in commonly owned, copending patent application Ser. No. 09/212,580 filed on Dec. 14, 1998, and Ser. No. 60/116,836 filed on Jan. 22, 1999 by Macoviak et al. Furthermore, technology has also been developed which incorporates suction to eliminate emboli after release of an external cross clamp. U.S. Pat. No. 5,697,905 to d'Ambrosio discloses a triple lumen intra-aortic balloon catheter which reduces the release of embolized air and particulate matter into the general body circulation, and WO 99/04848 to Maahs discloses an arterial aspiration catheter to be used in a blood vessel. However, none of these techniques address hypoperfusion.

Furthermore, developments in the area of minimally invasive cardiac surgery (MICS) and the use of balloon catheters to address the clinical problems associated with a traditional median sternotomy and the attendant use of a cross clamp to occlude the ascending aorta have been expanded. For example, U.S. Re Pat. No. 35,352 to Peters describes a single balloon catheter for occluding a patient's ascending aorta and a method for inducing cardioplegic arrest. A perfusion lumen or a contralateral arterial cannula is provided for supplying oxygenated blood during cardiopulmonary bypass. U.S. Pat. No. 5,584,803 to Stevens et al. describes a single balloon catheter for inducing cardioplegic arrest and a system for providing cardiopulmonary support during closed chest cardiac surgery. A coaxial arterial cannula is provided for supplying oxygenated blood during cardiopulmonary bypass. However, the occlusion balloon of these catheters must be very carefully placed in the ascending aorta between the coronary arteries and the brachiocephalic artery, and the position of the catheter must be continuously monitored to avoid complications.

In clinical use, these single balloon catheters have shown a tendency to migrate in the direction of the pressure gradient within the aorta. More specifically, during infusion of cardioplegia, the balloon catheter will tend to migrate downstream due to the higher pressure on the upstream side of the balloon and, when the CPB pump is on, the balloon catheter will tend to migrate upstream into the aortic root due to the higher pressure on the downstream side of the balloon. This migration can be problematic if the balloon migrates far enough to occlude the brachiocephalic artery on the downstream side or the coronary arteries on the upstream side.

Other developments in minimally invasive cardiac surgery include off-pump procedures. For example, U.S. Pat. Nos. 5,888,247 and 5,875,782 describe methods and devices for performing coronary artery bypass grafting on a beating heart. This approach is deemed beneficial in that it eliminates the complications of an external CPB machine, however this technique does not address how to protect the brain when an embolic event does occur.

Still other related technology involves cardiopulmonary support by selective aortic perfusion. U.S. Pat. Nos. 5,308,320, 5,383,854, 5,820,593, 5,906,588 by Peter Safar, S. William Stezoski, and Miroslav Klain describe a balloon catheter for segmenting a patient's aorta for selective perfusion of different organ systems within the body. Other US patent applications which address the concept of selective aortic perfusion include commonly owned, copending patent application Ser. No. 08/909,293, filed Aug. 11, 1997; and Ser. No. 09/152,589 filed Aug. 11, 1998 to Safar et al.

Furthermore, U.S. Pat. Nos. 5,738,649, 5,827,237, 5,833,671; and commonly owned, copending patent application Ser. No. 09/060,412, filed Apr. 14, 1998 by John A. Macoviak; and Ser. No. 08/665,635, filed Jun. 17, 1996; by John A. Macoviak and Michael Ross; and Ser. No. 60/067,945, filed Dec. 8, 1997, by Bresnahan et al. and Ser. No. 60/084,835, filed Apr. 25, 1997 by Macoviak et al. describe circulatory support systems and methods of use for isolated segmental perfusion. Selective perfusion can be used to prioritize the flow of oxygenated blood or other protective fluids to the various organ systems, with different temperatures, chemical compositions, flow rates and pressures to achieve optimal preservation of all organ systems within the body. These and all other patents and patent applications referred to herein are hereby incorporated by reference.

Although the previous inventions have made significant strides toward improving outcomes related to CPB surgery, there is still need for improvement. Therefore, what has been needed and previously unavailable is a method and apparatus for reducing the release of embolic material into the general blood circulation, while at the same time maintaining appropriate perfusion flow to avoid hypoperfusion and cerebral ischemia. The present invention solves these immediate problems, can be used in conjunction with much of the above-described technology, and solves other problems as well.

SUMMARY OF THE INVENTION

In keeping with the foregoing discussion, the present invention provides methods, systems and devices for performing cardiopulmonary bypass (CPB), cardioplegic arrest, suction of fluid from the aorta to remove embolic or other fluid from the general circulation and the selective segmentation of the arterial system to perform differential perfusion eliminating hypoperfusion. Provided is an aortic catheter having a catheter shaft and at least one occlusion member. In a preferred embodiment, a first occlusion member is expandable from the catheter shaft and a second occlusion member is expandable from the catheter shaft and is positioned distal to the first occlusion member. An arch lumen extends at least in part along the length of the catheter shaft and has a proximal opening coupled to a CPB machine and a distal arch opening located between the first occlusion member and the second occlusion member to provide fluid flow therebetween. A corporeal lumen extends at least in part along the length of the catheter shaft and has a proximal opening coupled to a CPB machine and a distal opening downstream of the second occlusion member to provide fluid flow distal to the second occlusion member. A suction lumen extends at least in part along the length of the catheter shaft and has a proximal suction opening coupled to a suction source and a distal suction opening residing in the aortic lumen of a patient.

The aortic catheter as described above may be combined with other devices to create a catheter system which may include a CPB machine, a suction source, various switches and a venous cannula/catheter to perform complete bypass, partial bypass and antegrade or retrograde fluid flow. Furthermore, the system may also be used in a number of different operating modes, including: stopped heart catheter procedures, concurrent surgical interventions and catheter based interventions, sequential surgical interventions, catheter based interventions and as a safety backup or bail out system in beating heart catheter procedures. The system provides cardiopulmonary support for the patient's circulatory system and prioritized protection for the patient's cerebral and corporeal circulation.

In one illustrative embodiment, an aortic catheter is provided having two occlusion members mounted on a catheter shaft which are sized and configured to substantially occlude the aorta and enable the selective management and perfusion of the myocardial, cerebral and corporeal circulations. The catheter is introduced through the ascending aorta and is navigated transluminally until the first occlusion member is positioned between the brachiocephalic artery and the coronary arteries and the second occlusion member is positioned downstream of the left subclavian artery. A corporeal lumen has a distal corporeal opening that is sized and configured to provide blood flow downstream of the second occlusion member at a flow rate that is sufficient to sustain appropriate metabolic demands of the corporeal body. An arch lumen has a distal arch opening that is sized and configured to provide blood flow downstream of the first occlusion member at a flow rate that is sufficient to sustain the life preserving metabolic demands of the cerebral circulation. A suction/cardioplegia lumen has a distal suction/cardioplegia opening that is sized and configured to provide cardioplegia, heart arresting fluid or heart therapeutic fluid to the myocardium, as well as provide aspiration of the aortic root upstream of the first occlusion balloon.

In another illustrative embodiment, an aortic catheter is provided having an outer tubular member and an inner tubular member that are arranged in a coaxial relationship. The inner tubular member is slidably disposed within the outer tubular member and is completely removable therefrom or alternatively may be built as an integral assembly that is nevertheless moveable relative to the outer tubular member. When the inner tubular member is completely removed or partially withdrawn, the outer tubular member may be used as an introducer cannula for the insertion of the inner tubular member or any other catheter or medical device. Alternatively, the outer tubular member may be used as a stand alone device in combination with an external cross-clamp, or other occlusion catheter by expanding the first occlusion member to occlude the aorta and having a flow lumen of sufficient size to provide adequate fluid flow to the cerebral and corporeal systems.

A single occlusion member mounted on the inner tubular member is sized and configured to substantially occlude the aorta to enable the selective management and perfusion of the cerebral and corporeal circulations. The catheter is configured for antegrade introduction through the ascending aorta and is navigated transluminally until the occlusion member is downstream of the left subclavian artery. The coaxial design creates an annular space that defines an arch lumen. The arch lumen has a distal arch opening that is sized and configured to provide blood flow upstream of the occlusion member at a flow rate that is sufficient to sustain life preserving metabolic demands of the cerebral circulation. In addition, the arch lumen is configured for aspirating the area downstream of the aortic valve. A corporeal lumen has a distal corporeal opening that is sized and configured to provide blood flow downstream of the occlusion member at a flow rate that is sufficient to sustain the metabolic demands of the corporeal body.

In another embodiment an aortic catheter is provided having two occlusion members mounted on a coaxial catheter shaft. A first occlusion member is mounted on an outer tubular member and a second occlusion member is mounted on an inner tubular member that is slidably disposed within the outer tubular member. The inner tubular member is designed to be completely removed from the outer tubular member or alternatively may be built as an integral assembly that is nevertheless moveable relative to the outer tubular member. When the inner tubular member is completely removed or partially withdrawn, the outer tubular member may be used as an introducer cannula for the insertion of the inner tubular member or any other catheter or medical device. Alternatively, the outer tubular member may be used as a stand alone device with the elimination of the external crossclamp by inflating the occlusion member to occlude the ascending aorta and having a flow lumen of sufficient size to provide adequate fluid flow to the cerebral and corporeal systems.

When used in conjunction with an inner tubular member having a second occlusion member, the inner tubular member is configured to be navigated transluminally until the second occlusion member is positioned downstream of the left subclavian artery so that the cerebral, myocardial and corporeal circulations are isolated. The coaxial configuration of the inner and outer tubular member creates an annular space that defines an arch lumen. The arch lumen has a distal arch port that is sized and configured to provide blood flow downstream of the first occlusion member at a flow rate that is sufficient to sustain life preserving metabolic demands of the arch circulation. A corporeal lumen has a corporeal port that is sized and configured to provide blood flow downstream of the second occlusion member at a flow rate that is sufficient to sustain appropriate metabolic demands of the corporeal body. A suction/cardioplegia lumen extends through the outer tubular member and is in fluid communication with a distal suction/cardioplegia opening that is in fluid communication with the aortic root such that cardioplegia delivery and aspiration of the aortic root is possible upstream of the first occlusion member.

A system for performing CPB is disclosed which incorporates a venous cannula for withdrawing fluids from a vessel into a CPB machine, a left ventricle cannula for venting the left ventricle, a cardiotomy suction cannula for removing blood from the surgical field, and an arterial cannula having two occlusion members configured to segment the aorta and to provide differential perfusion to the cerebral circulation and the corporeal circulation and also to provide for the delivery of cardioplegia and aspiration of the aortic root.

A system for performing CPB is also provided having an aortic cannula/catheter configured for segmenting the aorta into various subsystems, a venous cannula/catheter configured for segmenting the venous system into various subsystems, a coronary sinus catheter, a therapeutic catheter and a switching mechanism. The present system is configured for complete isolation of the myocardial, cerebral and corporeal circulations, for antegrade, retrograde and/or alternating retrograde, antegrade perfusion to the cerebral circulation and antegrade, retrograde and/or alternating antegrade and retrograde cardioplegia delivery to the myocardium. Furthermore the present invention has a fluid instrument lumen configured for cardioplegia delivery, aspiration and for receiving a second therapeutic catheter, drug delivery catheter or fiber-optic catheter. The aortic catheter is configured for retrograde introduction into the patient's aorta via a peripheral arterial access point, such as the femoral artery. Alternatively, the aortic catheter may be configured for central approach without departing from the scope of the invention.

A venous drainage catheter system is provided that is configured for central introduction or alternatively through the femoral vein or other suitable venous access point in the lower extremities. Alternatively, the dual lumen venous drainage cannula may be configured for introduction though the patient's superior vena cava via the jugular vein or other suitable venous access point in the neck or upper extremities.

The venous drainage cannula system includes a first occlusion balloon or other expandable occlusion member mounted on a first tubular shaft, which is positioned within the patient's superior vena cava when in the operative position, and a second occlusion balloon or other expandable occlusion member, mounted on a second tubular shaft, which is positioned within the patient's inferior vena cava when in the operative position. Alternatively, a single catheter can be used with two occlusion balloons mounted on the catheter shaft. When the venous drainage catheter is configured for femoral artery introduction, the first occlusion balloon is mounted near the distal end of the tubular shaft and the second occlusion balloon is mounted somewhat proximal to the first balloon. Alternatively, for jugular vein introduction, these positions are reversed.

Venous blood from the head and upper extremities enters the patient's superior vena cava and is drained out through the first venous drainage lumen of the venous drainage catheter as the first occlusion balloon prevents blood from traveling into the right atrium from the superior vena cava. The blood is oxygenated, cooled and recirculated by the first blood circulation system to the head and upper extremities through the arch perfusion lumen of the arterial cannula.

The corporeal loop of the circulatory support system is created by having a venous drainage port in fluid communication with the inferior vena cava drainage lumen. Optionally, vacuum assist may be used to enhance venous drainage through the second venous drainage lumen of the venous drainage cannula. Venous blood from the viscera and lower extremities enters the patient's inferior vena cava and is drained out through the second venous drainage lumen of the venous drainage cannula. The blood is oxygenated, cooled and recirculated by the second blood circulation system to the viscera and lower extremities through the corporeal perfusion lumen of the arterial catheter.

Alternatively, the venous drainage cannula may be provided with a third venous drainage lumen within the tubular shaft connected to the drainage ports between the first and second balloons for draining the patient's right atrium and the coronary sinus. A separate coronary perfusion loop can be created by connecting the third venous drainage lumen to the inflow of a third blood circulation pump and connecting the outflow of the pump to the cardioplegia lumen of the arterial cannula. The third blood circulation pump may be a peristaltic roller pump, a centrifugal blood pump or other suitable blood circulation pump. Preferably, the coronary loop also includes a venous blood reservoir, a blood oxygenator and heat exchanger in series with the third blood circulation pump.

As another alternative, the coronary circulation can be isolated by using a coronary sinus catheter for retrograde or antegrade administration of cardioplegia into the patient s coronary arteries with complete isolation of the myocardium. A separate coronary perfusion loop can be created by connecting the coronary sinus lumen to the inflow of a third blood circulation pump and connecting the outflow of the pump to the cardioplegia lumen of the arterial cannula. The third blood circulation pump may be a peristaltic roller pump, a centrifugal blood pump or other suitable blood circulation pump.

Furthermore, the system of the present invention is equipped with a switching mechanism that is used to provide either antegrade flow or retrograde flow, or may be used to alternate between retrograde flow and antegrade flow as the surgical procedure dictates.

Methods are provided which include providing an aortic catheter having a catheter shaft having a distal portion, and a corporeal lumen which extends at least in part along the length of the catheter shaft and opens as at least one distal corporeal opening. An arch lumen extends at least in part along the length of the catheter shaft and opens as at least one distal arch opening. An occlusion member is expandable from the aortic catheter residing between the distal corporeal opening and the distal arch opening. A suction switch, having a first position and a second position is configured for converting the arch lumen to a suction lumen. The distal portion of the aortic catheter is inserted into a patient's ascending aorta and is navigated transluminally through the aorta until the occlusion member is positioned in the ascending aorta upstream of the brachiocephalic artery. The occlusion member is expanded to resist or to occlude blood flow in the patient's ascending aorta. Heart arresting material is delivered to the heart of the patient to at least partially arrest the heart and the catheter shaft is navigated until the occlusion member is located in the descending aorta downstream of the left subclavian artery. Blood is perfused at a first temperature upstream from the occlusion member through the arch perfusion lumen and blood is perfused at a second temperature downstream of the occlusion member through the corporeal lumen. The suction switch may be activated at any time during the surgical procedure to evacuate fluid from the aorta.

In addition to the above method, a coronary sinus catheter may be provided to provide retrograde perfusion to the myocardium and a venous cannula may also be provided in conjunction with a switch to enable retrograde delivery to the cerebral circulation while the arterial catheter serves as a means for withdrawing fluid.

BRIEF DESCRIPTION OF THE DRAWINGS

FIG. 1 illustrates a side view of the aortic catheter of the present invention configured for antegrade deployment and capable of differential perfusion, cardioplegia delivery and aspiration.

FIG. 2 is a magnified lateral crosssection of the aortic catheter of FIG. 1 taken along line 2—2 of FIG. 1.

FIG. 3 is a magnified lateral cross-section of the aortic catheter of FIG. 1 taken along line 3—3 of FIG. 1.

FIG. 4 is a magnified lateral cross-section of the aortic catheter of FIG. 1 taken along line 4—4 of FIG 1.

FIG. 5 is a magnified lateral cross-section of the aortic catheter of FIG. 1 taken along line 5—5 of FIG. 1.

FIG. 6 is an in situ illustration of an embodiment of the present invention with part of the aorta cut away for illustrating placement of the aortic catheter.

FIG. 7 illustrates a side view of the aortic catheter of the present invention configured for antegrade deployment and capable of differential perfusion, aspiration and slidable movement of an inner tubular member.

FIG. 8 is a magnified lateral cross-section of the aortic catheter of FIG. 7 taken along line 8—8 of FIG. 7 illustrating the coaxial configuration of the inner tubular member and outer tubular member.

FIG. 9 is a magnified lateral cross-section of the aortic catheter of FIG. 7 taken along line 9—9 of FIG. 7 illustrating the lumen configuration of the inner tubular member.

FIG. 10 is a magnified lateral cross-section of the aortic catheter of FIG. 7 taken along line 10—10 of FIG 7.

FIG. 13 is a longitudinal cross section of the aortic catheter of FIG. 7.

FIG. 14 is an in situ illustration of an embodiment of the present invention with part of the aorta cut away for illustrating placement of the aortic catheter.

FIG. 22 is an in situ illustration of the aortic catheter of FIG. 17 with part of the aorta cut away for illustrating placement of the aortic catheter.

FIG. 28A is a schematic drawing illustrating the various components of a switching assembly.

FIG. 28B is a schematic drawing illustrating the various components of a switching assembly.

DETAILED DESCRIPTION

Figure 11A:
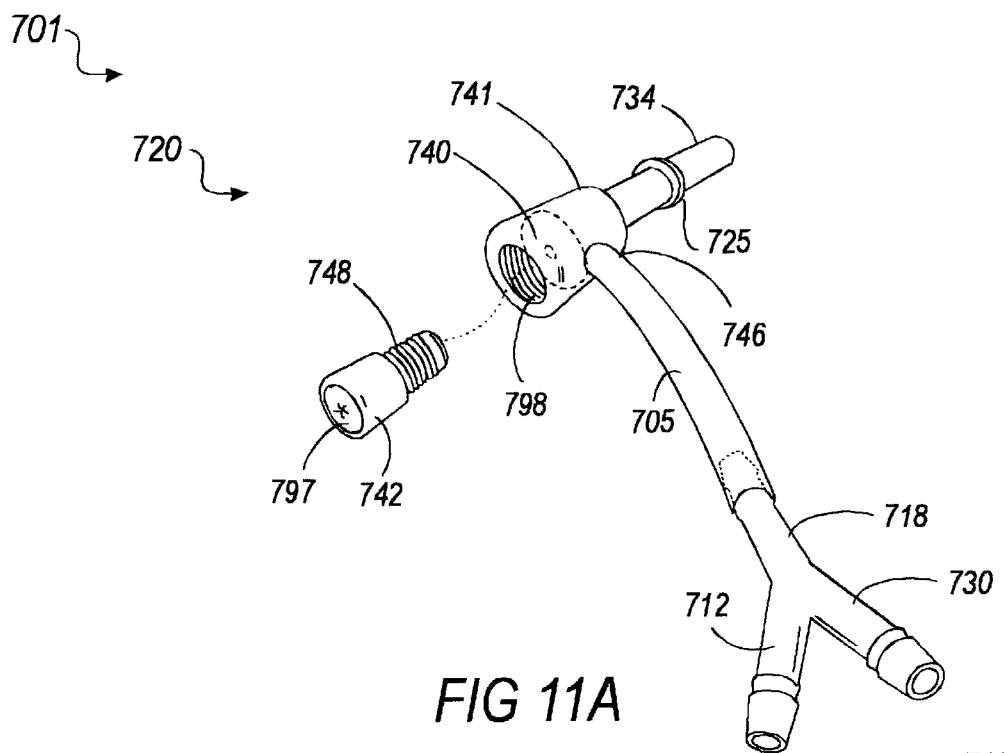
FIGS. 11A and 11B illustrate the aortic catheter of FIG. 7 with the inner tubular member completely removed from the outer tubular member and manifold assembly.

The detailed description set forth below in connection with the drawings is intended merely as a description of the presently preferred embodiments of the invention, and is not intended to represent the only form in which the present invention may be constructed or utilized. The description sets forth the design, functions and methods of implementing the invention in connection with the illustrated embodiments. It is to be understood, however, that the same or equivalent functions and sequences may be accomplished by different embodiments that are also intended to be encompassed within the spirit and scope of the invention. The illustrated embodiments of the present invention are for use in the course of performing conventional open chest or minimally invasive cardiopulmonary bypass (CPB).

FIGS. 1 through 5 illustrate an embodiment of the aortic catheter 101 of the present invention, configured for antegrade deployment and adapted to enable suction and differential perfusion. As used herein, differential perfusion or to perfuse differentially is the ability of the clinician to isolate separate organ systems as a means for separately controlling temperature, pressure, flow and chemical composition. FIG. 1 illustrates a side view of the aortic catheter 101. FIG. 2 is a magnified lateral cross section of the aortic catheter 101 taken along line 2—2 in FIG. 1. FIG. 3 is a magnified lateral cross section of the aortic catheter 101 taken along line 3—3 in FIG. 1. FIG. 4 is a magnified lateral cross section of the aortic catheter 101 taken along line 4—4 in FIG. 1. FIG. 5 is a magnified lateral cross section of the aortic catheter 101 taken along line 5—5 in FIG. 1.

Referring now to FIG. 1, the aortic catheter 101 has a shaft portion 150 and a manifold portion 160. A catheter shaft 102 has a proximal end 126 and a distal end 127 and is of sufficient length to reach from an arterial insertion point to a patient's descending aorta. With the aforementioned length requirement in mind, the catheter shaft is preferably between 2 and 30 cm, more preferably between 7 and 20 cm, most preferably between 12 and 15 cm.

As shown in FIG. 2, the catheter shaft contains a suction/cardioplegia lumen 111, which opens as at least one, preferably 1 to 15 distal suction/cardioplegia openings 113. The arch lumen 105, the corporeal lumen 108, the first inflation lumen 114 and the second inflation lumen 115, all continue through the catheter shaft 102 while the first inflation lumen 114 opens at a first distal inflation port(s) 122 and the arch lumen 105 terminates at a distal arch opening(s) 107.

As shown in FIG. 3, four of the five lumens continue distally through the shaft 102 beyond the distal suction/cardioplegia opening 113, the arch lumen 105, the corporeal lumen 108, the first inflation lumen 114 and the second inflation lumen 115. As shown in FIG. 4, two lumens continue distally through the elongated shaft 102 beyond the distal inflation port 122 and the distal arch openings 107, the corporeal lumen 108, and the second inflation lumen 115. As shown in FIG. 5, only the corporeal lumen 108, continues distally through the elongated catheter shaft 102 beyond the distal inflation port 128 and terminates as one or more distal corporeal openings 110 preferably approximately 1 to 20 openings.

FIGS. 1 through 5 collectively illustrate the distally tapering configuration of the outer diameter of the elongated catheter shaft 102. This shape is especially conducive for facilitating direct penetration of the vessel wall and gentle dilation of the puncture site, limiting trauma to the tissue of the aorta. Alternatively, when a purse string suture and subsequent aortotomy incision is implemented, the aforementioned configuration promotes the sealing of the aortotomy site since the gradual increase in outer diameter in the proximal direction enables full closure of the aortotomy incision. For use in adult human patients the smallest outer diameter, near the distal tip 116 is from approximately 9 to 30 French (3.0–10.0 mm diameter), more preferably from approximately 12 to 26 French (4.0–8.6 mm diameter). Catheters for pediatric patients and porcine models may be relatively smaller. Furthermore, the catheter shaft has a preshaped S-configuration angled out of plane to represent the aortic arch anatomy of a human being as illustrated in connection with FIG. 6.

The catheter shaft 102 is preferably formed of a flexible thermoplastic material, a thermoplastic elastomer or a thermoset elastomer. To create the gradually tapering catheter shaft 102 of FIG. 1, separate tubing pieces, having the desired lumen configuration, may be attached end to end and bonded together by methods such as heat welding or adhesive bonding. Alternatively, an end of tubing can be skived away and a TEFLON coated or other lubricous coated mandrel may be used to promote insertion of one tubing piece into another. The use of UV adhesive bonding and shrink tubing with heat application may be incorporated to ensure that assembled pieces are sealed fluid tight. Alternatively, the catheter shaft 102 may be fabricated by dipping or by composite construction techniques and joined together or the entire catheter shaft 102 may be fabricated integrally. Furthermore, the use of tapered mandrels and a heat source can be used to neck down the outer diameter of the catheter shaft. In alternative embodiments, where it is desirable to have a catheter shaft with one continuous outer diameter, a single piece of tubing can be extruded and necked down to proper dimensions. Suitable materials for the elongated catheter shaft 102 include, but are not limited to, PEBAX, PVC, PET, polystyrene, polyvinylchloride, polyurethane, polyethylene, polypropylene, polyamides (nylons), copolymers polyesters, silicone, latex, and combinations thereof, as well as braided, coiled or counterwound wire or filament reinforced composites. Alternatively, the catheter shaft may be made of thin walled metallic tubing, such as stainless steel, platinum, titanium, nitinol, alloys, cobalt alloys such as Elgiloy and Carpenter MP 35.

The aortic catheter 101 may be coated with lubricious coatings that aid in the insertion and removal of the catheter as well as aid in hemocompatibility and anticoagualtion, the coatings are nonreactive and hydrophilic or hydrophobic. Medicated coatings may also be incorporated which are antithrombogenic, antimicrobial, anticancer, antigrowth factor, growth factor or anti-inflamatory. Examples of such coating are SLIP-COAT and MEDI-COAT made by STS Polymers Henrietta, N.Y. In addition, the shaft may be coated with echogenic material such as ECHO-COAT also made by STS Polymers Henrietta, N.Y. to aid in tracking and placement of the device with the use of ultrasound.

The aortic catheter has fittings attached to the proximal end of the catheter shaft 102, which are in fluid communication with an extracorporeal circuit. The tube fittings are attached to the catheter shaft 102 with UV adhesive, cyanoacrylate, heat bonding or solvent bonding. A manifold cover 120 is made of a durable material such as polycarbonate, nylon or any other nylon or polymer suitable to protect the bonding joints, which can be easily damaged through inadvertent surgical clamping or manipulation of the tubing. The manifold cover 120 may be molded, insert molded, heat shrink, or any other suitable material and fabrication for protecting the bonding joints.

The arch lumen tube fitting 105' has a proximal arch opening 106 coupled to a barb connector 118 or other suitable fitting capable of being coupled to a CPB machine. The corporeal lumen tube fitting 108' has a proximal corporeal opening 109 coupled to a barb connector 117 or other suitable fitting capable of being coupled to a CPB machine. The suction/cardioplegia lumen tube fitting 111' has a proximal opening 112 connected to a Y-fitting 119 that has a barb connector 131 other suitable fitting for coupling to a cardioplegia source and a second barb connector 130 or other suitable fitting capable of being coupled to a suction source. The first actuating lumen 114, in this exemplary embodiment taking the form of an inflation lumen, has a tube fitting 114' that is in fluid communication with a proximal opening 132 connected to a stopcock 134, or other suitable fitting for connection to a syringe or other inflation source. The second actuating lumen 115, in this exemplary embodiment taking the form of a second inflation lumen, has a tube fitting 115' in fluid communication with a proximal opening 133 connected to a stopcock 135, or other suitable fitting for connection to a syringe or other actuating source. Alternatively, a single actuating lumen may be implemented to actuate both occlusion members.

A first occlusion member 103, in this exemplary embodiment in the form of an occlusion balloon, is located on the catheter shaft 102 proximal to the distal end 127 and is in fluid communication with the first distal inflation port/opening(s) 122 residing in the interior of the first occlusion member 103 configured for receiving fluid or other inflation material through the first inflation lumen 114. The first occlusion member 103 is designed and configured to have an uninflated state and an inflated state 103'. In the uninflated state the occlusion member 103 is particularly suited for ease of entry into a vessel. In the inflated state 103' the occlusion member 103 is expanded from the catheter shaft 102, and is capable of preventing all or substantially all blood flow in the ascending aorta. For use in adult human patients, the first occlusion member 103 preferably has an inflated outer diameter of approximately 1.5 cm to 5.0 cm, but may be larger or smaller as any given procedure may dictate. Preferably, the first occlusion member 103 has an inflated length that is not significantly longer than its inflated diameter, or, more preferably, is shorter than its inflated diameter. This shortened inflated profile allows the first occlusion member 103 to be easily placed within the ascending aorta between the coronary arteries and the brachiocephalic artery without any danger of inadvertently occluding either. Suitable materials for the first occlusion member 103 include the same materials as described for the catheter shaft and flexible polymers, thermoelastomers and elastomers, which include, but are not limited to, polyvinylchloride, polyurethane, polyethylene, polypropylene, polyamides (nylons), polyesters, latex, silicone, and alloys, copolymers and reinforced composites thereof. The first occlusion balloon may be eccentric, concentric, oblong, round, oval, teardrop shaped, porous, non-porous, part porous-part non-porous or any combination thereof. Furthermore, the balloon is attached to the catheter shaft by bonding, UV adhesive, ultrasonic welding, heat bonding, solvent boding, cyanoacrylate or mechanical bonds by way of a friction, press fit, external compression or filament winding or any other attachment means.

A second occlusion member 104, in this exemplary embodiment in the form of an occlusion balloon, is located on the catheter shaft 102 distal to the first occlusion member 103 and is in fluid communication with the second distal inflation port/opening(s) 128 residing in the interior of the second occlusion member 104 for receiving fluid or other inflation material through the second inflation lumen 115. The second occlusion member has an expandable position 104' and an unexpanded position 104, and is positioned distal to the first occlusion member 103 at a distance preferably between 3 and 20 cm, more preferably between 8 and 15 cm. The distance is determined such that when the first occlusion member 103 is positioned within the ascending aorta between the coronary arteries and the brachiocephalic artery, the second occlusion member 104 will be positioned in the descending aorta downstream of the left subclavian artery. The second occlusion member 104 may be more elongated than the first occlusion member 103 since distal placement of the balloon past the left subclavian artery is possible and there is more room for the balloon to expand longitudinally without occluding spinal cord blood flow. In addition, suitable materials for the second occlusion member 104 include the same materials for the catheter shaft or the first occlusion member in addition to flexible polymers, thermoelastomers and elastomers, which include, but are not limited to, polyvinylchloride, polyurethane, polyethylene, polypropylene, polyamides (nylons), polyesters, latex, silicone, and alloys, copolymers and reinforced composites thereof. Furthermore, the balloon is attached to the catheter shaft 102 by bonding, UV, ultrasonic welding, heat bonding, solvent boding, cyanoacrylate or mechanical bonds by way of a friction, press fit, external compression or filament winding or any other attachment means.

Optionally, the outer surface of the second occlusion member 104 or the first occlusion member 103 may be manufactured to include a friction increasing coating or texture to increase friction with the aortic wall when deployed. Other variations describing balloon characteristics, made be found in, and reference is made to, commonly owned copending application Ser. No. 09/205,753 filed on Dec. 4, 1999 and Ser. No. 09/205,753 filed May 8, 1999 which are hereby incorporated by reference in their entirety.

The suction/cardioplegia lumen 111 extends from the proximal suction/cardioplegia opening 112 through the catheter shaft 102, to at least one distal suction/cardioplegia opening 113 on the exterior of the catheter shaft 102 proximal to the first occlusion member 103. The distal suction/cardioplegia opening(s) 113 can take the form of a single opening, two openings, or multiple openings, however primary importance is given to optimal flow, suction and pressure characteristics. The exact termination position may vary; however, the opening should be in a position that optimizes the ability aspirate fluid from the aorta and also facilitates the delivery of cardioplegia to the myocardium at certain intervals.

The arch lumen 105 extends from the proximal arch opening 106 through the catheter shaft 102, to at least one distal arch opening(s) 107 on the exterior of the catheter shaft 102 distal to the first occlusion member 103 and proximal to the second occlusion member 104. The distal arch opening(s) 107 can take the form of a single opening, two openings, or multiple openings, however the distal arch opening 107 is sized and configured to provide optimal flow and pressure to maintain the metabolic demands of the cerebral circulation.

The corporeal lumen 108 extends from the proximal arch opening 109 through the catheter shaft 102 to at least one distal corporeal opening(s) 110 on the exterior of the catheter shaft 102 downstream from the second occlusion member 104. The distal corporeal opening(s) 110 may take the form of a single opening, a single opening with a blood diffuser or multiple openings to provide optimal flow and pressure to maintain the metabolic demands of the corporeal circulation.

The first inflation lumen 114 extends from a first proximal actuating opening 132 through a first pressure monitoring balloon 123 and through the catheter shaft 102 to a first distal actuating port 122, within the first occlusion member 103. The second inflation lumen 115 extends from the second proximal actuating opening 133 through the second pressure monitoring balloon 145 and through the catheter shaft 102 to a second distal actuating port 128 within the second occlusion member 104. The first and second pressure monitoring balloons are designed to give the clinician tactile feedback for determining if the occlusion members are inflated. The pressure monitoring balloons may be made from flexible polymers, thermoelastomers and elastomers, which include, but are not limited to, polyvinylchloride, polyurethane, polyethylene, polypropylene, polyamides (nylons), polyesters, latex, silicone. Alternatively, inflation pressure may be monitored or regulated with a pressure relief valve, pressure release valve, elastomer, metal or spring loaded bellows rated springs or spring or any combination thereof.

The catheter shaft 102 may include one or more markers, in the form of radiopaque markers and/or sonoreflective markers or alternatively or in combination may have echogenic material coatings to enhance imaging of the catheter shaft 102 using fluoroscopy or ultrasound, such as transesophageal echocardiography (TEE). Alternatively, or in addition thereto, the catheter can be configured to have magnets imbedded or placed on the catheter shaft 102 such that a sensing means detects the location of the catheter shaft 102 by sensing the static magnetic field strength gradient produced by the magnet associated with the catheter shaft 102. Optionally, these magnets can be placed within or on the occlusion members to indicate their proper position for deployment. Alternatively, a locator lumen may be provided for receiving a fiber optic device or other instrument for delivering ultraviolet light, visible light, near infrared light, or infrared light from a radiation source. Alternatively, the fiber optic device may be built integrally within the catheter. Alternatively a fiberoptic device may be inserted through the first and second inflation lumens through the catheter shaft 102 within the interior of the first and second occlusion balloons such that the illumination can indicate the position of the balloons. In this illustrative embodiment, the aortic catheter 101 includes radiopaque markers 121 positioned within the first and second occlusion member 103 and 104 respectively. The radiopaque markers may be made of a ring of dense radiopaque metal, such as gold, platinum, tantalum, tungsten or alloys thereof, or a ring of a polymer or adhesive material heavily loaded with a radiopaque filler material.

The distal tip 116, located adjacent the distal end of the catheter shaft 102, may be made from the same materials as the catheter shaft or alternatively, the distal tip 116 may be made of a different material than catheter shaft 102. For example, the distal tip 116, the distal region of the catheter shaft 102 or the majority of the catheter shaft, may be made of a temperature sensitive polyurethane such as TECOFLEX or TECOPHILIC such that when the tip is exposed to a colder environment, the material becomes more rigid and is easily insertable into the ascending aorta while having the ability to become more pliable when exposed to the warmer temperature of body fluids. One method of achieving the desired results is to place the distal tip 116 in a 4-degree saline solution preoperatively to rigidify the tip, then inserting the catheter 101 through the aortic wall. Once in the warmer of the aortic lumen, the distal tip softens due to the material composition and temperature sensitivity. Furthermore, the distal tip 116 may have multiple distal corporeal openings 110 to reduce fluid velocity through the distal corporeal openings 110. Alternatively, the distal tip may have a distal corporeal opening with a diffuser to reduce the "sandblasting" effect on the aortic wall.

The aortic catheter 101 further includes depth markers 124 so the surgeon can determine the depth of the catheter shaft 102 inside the patient's anatomy. Optionally, a cranial orientation line may be provided to insure that the curvature of the catheter shaft is properly oriented in the aorta. When the appropriate depth has been confirmed, the suture ring 125, which is slidably mounted on the catheter shaft 102, can be adjusted to seat against the exterior of the tissue in order to better seal and keep the catheter shaft 102 in place during the surgical procedure and to secure the purse string suture. Examples of various embodiments of suture rings and accompanying sealing mechanisms are found in commonly owned and copending patent application Ser. No. 09/158, 407 filed on Sep. 22, 1998, which is hereby incorporated by reference herein.

FIG. 6 illustrates another embodiment of the aortic catheter of the present invention deployed in a patient's aorta configured for antegrade deployment and capable of suction and differential perfusion. First, the patient's ascending aorta is accessed. Methods for introducing the aortic catheter into the ascending aorta include but are not limited to; a thoracoscopic access port, median sternotomy, rib-sparing minithoracotomy, thoracotomy with removal of ribs or costal cartilages, transverse sternotomy, or L-shaped, C-shaped and Z-shaped partial sternotomies as described in commonly owned, copending application Ser. No. 60/102,728 filed on Oct. 1, 1998, which is hereby incorporated by reference in its entirety. A purse string suture is completed in the wall of the ascending aorta followed by an aortotomy incision made inside of the purse string. Then, the aortic catheter 601 is introduced into the patient's ascending aorta through the aortotomy incision. Alternatively, the aortic catheter 601 may be introduced via the Seldinger Technique by using a needle and guidewire with or without an introducer sheath and dilator. Alternatively, the distal tip may be made from a temperature sensitive material such as TECOFLEX or TECOPHILIC such that when the tip is exposed to a colder environment, the material becomes more rigid and is easily insertable into the ascending aorta while having the ability to become more pliable when exposed to the warmer temperature of body fluids. One method of achieving the desired results is to place the distal tip 616 in a 4-degree saline solution preoperatively to stiffen the tip, then inserting the catheter 601 through the aortic wall. Once in the warmer of the aortic lumen, the distal tip softens due to the material composition and temperature sensitivity. Furthermore, the distal tip could be configured such that, in the stiffened state, the distal tip aids is creating and/or dilating the aortotomy incision.

Meanwhile, or previous thereto one or more venous cannulae are introduced into the vena cava by way of bicaval, single atrial, cavoatrial or similar approaches. Alternatively, venous cannulation of the femoral vein or the jugular vein may be used. The aortic catheter 601 is navigated transluminally through the ascending aorta and across the aortic arch under fluoroscopic, ultrasound, fiberoptic, magnetic guidance, or under direct visualization with the aid of depth markers 624. The aortic catheter 601 is advanced until the first occlusion member 603 is positioned within the ascending aorta between the coronary arteries and the brachiocephalic artery and the second occlusion member 604 is positioned in the descending aorta downstream of the left subclavian artery. When proper position is confirmed with reference to depth markers 624 or any of the aforementioned techniques, the movable suture ring 625 is adjusted into place to create a seal against the vessel wall and the purse string suture is secured thereto. Using a multihead cardiopulmonary bypass pump or the like, perfusion of oxygenated blood is started, exiting through the corporeal opening(s) 610 and the distal arch opening(s) 607 to take some of the pumping load off the heart. The first occlusion member 603 and the second occlusion member 604 are then inflated to partition the aorta, whereupon a cardioplegic agent, such as cold crystalloid cardioplegia, blood cardioplegia, or cold blood is infused through the suction/cardioplegia lumen 611 out of the distal suction/cardioplegia opening(s) 613 to induce partial or complete cardioplegic arrest. Alternatively, electrical or chemical nerve blocks may be used to at least partially arrest the heart. The sequence of inflating the balloons may be simultaneous or sequential depending upon the desired results. Alternatively, or in addition thereto, cardioplegia, retrograde cardioplegia and/or aspiration of the aortic root may be accomplished through a separate cardioplegia needle, catheter or through a retrograde coronary sinus catheter.

Differential perfusion is established giving the clinician the ability to regulate flow, and/or pressure, temperature or chemical composition to each of the segmented portions of the arterial system. According to one method normothermic blood is perfused to the corporeal circulation through the distal corporeal opening(s) 610 while perfusing hypothermic blood to the cerebral circulation through the distal arch opening(s) 607. This type of selected management gives the surgeon the ability to provide hypothermic protective qualities to the brain while at the same time providing the benefits of a normothermic perfusion to the body. In another embodiment cold or warm or normothermic perfusion to the body and brain may be desired and differential flow and pressure is accomplished by partial inflation of occlusion member 604. This second method effectively uses the second occlusion member 104 as a valve to regulate fluid flow past the second occlusion member 104. Differential perfusion gives the clinician the ability to regulate all subcirculations including the heart, brain and body separately and selectively. For a complete description of a multi-head pump, venous and arterial catheters capable of providing differential perfusion, reference is made to commonly owned, copending application Ser. No. 09/306,555 filed May 6, 1999, which is hereby incorporated by reference in its entirety. Cardioplegic arrest is maintained by continued infusion of a cardioplegia agent through the suction/cardioplegia lumen 611. Alternatively or in addition thereto, a surgeon may use a separate cardioplegia needle or catheter, or a retrograde coronary sinus catheter to infuse a cardioplegia agent for as long as necessary to complete the surgical procedure using standard open chest or minimally invasive techniques.

Perfusion temperatures, perfusate compositions and perfusion flow rates may be optimized to each of the segmented regions of the patient's circulation for optimal organ preservation during cardiopulmonary bypass. While the aortic catheter 601 is deployed, the second occlusion member 604 stabilizes and anchors the catheter shaft 602 and prevents upstream or downstream migration of the catheter 601 or the first occlusion member 603 due to differential pressures within the aorta. Alternatively, the second occlusion member 664 may be used as a valve in the descending aorta by partial inflation thereby controlling fluid flow at a certain rate. Furthermore, the shaft is sufficiently rigid to maintain the catheter in its proper position helping to keep the occlusion members in their proper positions.

Figure 24:
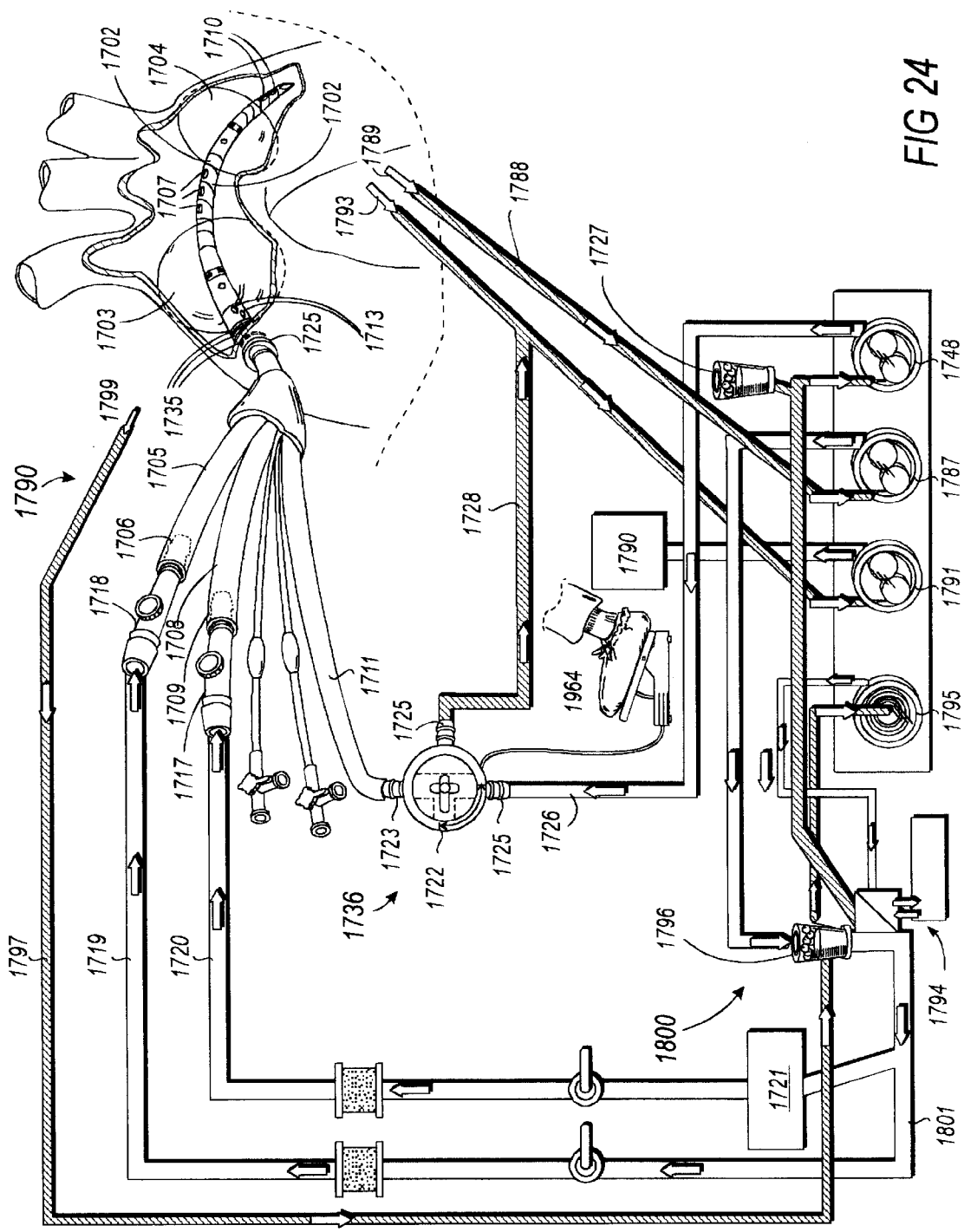
FIG. 24 is a schematic illustration of the catheter system of the present invention configured for suction and differential perfusion.

Ultrasound or other sensing mechanisms can be used during the surgical procedure to immediately determine when embolic events occur. By activating a switch, as illustrated in FIG. 24, the suction/cardioplegia lumen 611 is changed from a cardioplegia source to a suction source, enabling the withdrawal of fluid and embolic debris such as, gaseous bubbles, atheroma or thrombus from the region upstream of the first occlusion member 603 through the distal suction/cardioplegia opening 613. Alternatively, a lateral cannula may be employed. In addition, retrograde perfusion through the superior vena cava or central cerebral vein can be done by using a venous cannula/catheter to limit flow to the brain from the aortic arch, where embolic material may originate. At the completion of the surgical procedure, the first occlusion member 603 and the second occlusion member 604 are deflated to allow oxygenated blood to flow into the patient's coronary arteries, whereupon the heart should spontaneously resume normal sinus rhythm. Alternatively, only the first occlusion member 603 is deflated while continuing hypothermic perfusion to the brain and myocardium with or without suction. This procedure will delay normal sinus rhythm by keeping the myocardium cold through the cold blood perfusion while at the same time keep the protective properties of hypothermia to the brain. When the surgeon desires to restart the heart, suction may be applied prior to and at the inception of heart restart. Tepid oxygenated blood flow is allowed into the patient's coronary arteries, whereupon the heart should spontaneously resume normal sinus rhythm. If necessary, cardioversion or defibrillation shocks may be applied to restart the heart if the myocardium is unresponsive when normal sinus rhythm is desired. The patient is then weaned off bypass and the aortic catheter 601 and any other cannulae are withdrawn. At the end of the surgical procedure the patient has a cold brain, which extends postoperatively, and a normothermic body.

Alternatively, the second occlusion member 604 is deflated while blood or saline is perfused to the myocardium through a retrograde coronary sinus catheter while the suction/cardioplegia lumen aspirates the area upstream of the first occlusion member 603. This effectively flushes the coronary arteries and the area upstream of the first occlusion member 603. The brain is continued to be perfused with cold blood to maintain the protective qualities of hypothermia. After the coronaries and the aortic root have been flushed the first occlusion member 603 is deflated while aspiration continues. The patient is then weaned off bypass and the aortic catheter 601 and any other cannulae are withdrawn. At the end of the surgical procedure the patient has a cold brain, which extends postoperatively, and a normnothermic body.

Alternatively, the second occlusion member 604 is deflated and the corporeal flow is turned off or reduced while arch perfusion continues. Thereafter, the first occlusion member 603 is deflated and the patient is then weaned off bypass.

FIGS. 7 through 10 illustrate another embodiment of the aortic catheter of the present invention configured for antegrade deployment and adapted for differential perfusion and suction. FIG. 7 is a side view of the aortic catheter 701. FIG. 8 is a magnified lateral cross section of the aortic catheter 701 taken along the line 8—8 in FIG. 7. FIG. 9 is a magnified lateral cross section of the aortic catheter 701 taken along the line 9—9 in FIG. 7. FIG. 10 is a magnified lateral cross section of the aortic catheter 701 taken along the line 10—10 in FIG. 7.

Referring to FIG. 7, the aortic catheter 701 has a shaft portion 750 and a manifold portion 760. The shaft portion 750 is comprised of a catheter shaft 702 having an inner tubular member 733 and an outer tubular member 734 arranged in a coaxial configuration and such that the inner tubular member is slidably disposed within the outer tubular member 734. The inner tubular member 733 may be made from any number of materials such as polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, coil reinforcement may be achieved by embedding, laminating, or coextruding flat, round or square wire, helically wound wire or braided wire on or into the shaft material. The outer tubular member 734 may be made of the same materials as the inner tubular member 733, may or may not be coil reinforced and may be made from metals, alloys or rigid polymers such as polycarbonate, polysulfone or polyetherimide. The non-coaxial portion 780 has a preformed S-curvature specially designed to better reflect the patient's aortic anatomy. The catheter shaft 702 is of sufficient length to reach from an arterial insertion point to a patient's descending aorta. With the aforementioned length requirement in mind, the catheter shaft is preferably between 2 and 30 cm, more preferably between 7 and 20 cm, most preferably between 12 and 15 cm.

Figure 11B:
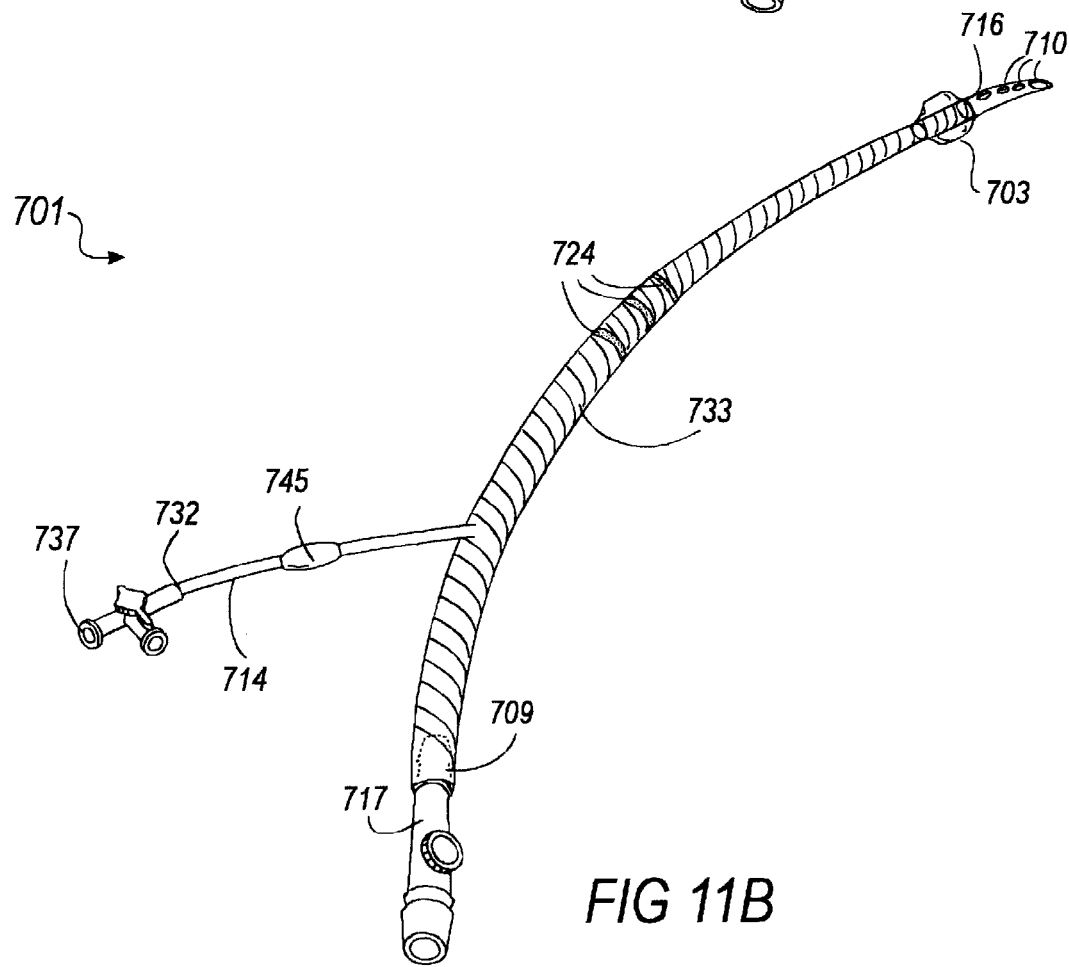
Figure 12A:
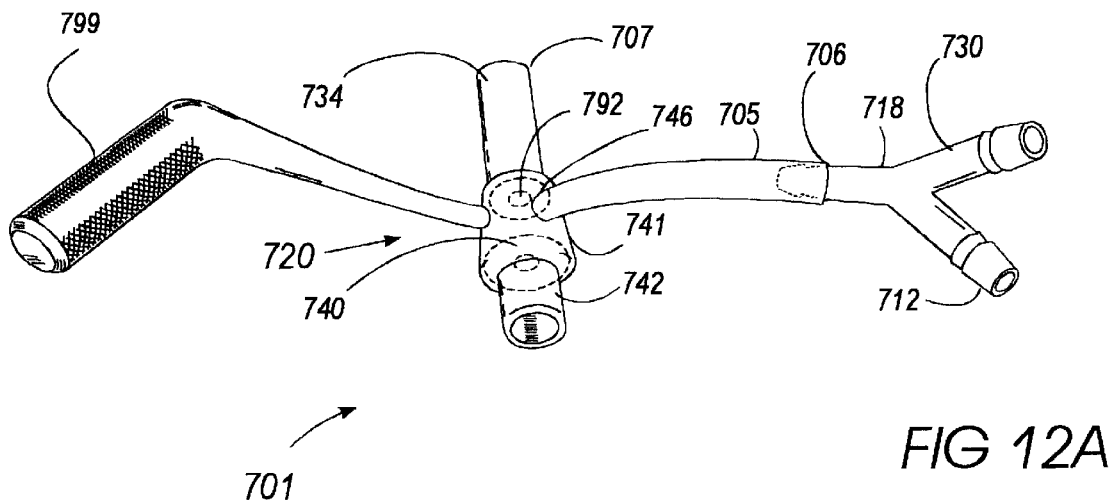
FIG. 12A is a side view of the manifold assembly and outer tubular member of FIG. 7 configured for receiving a second medical instrument or an inner tubular member and having a non-integral handle.
Figure 12B:
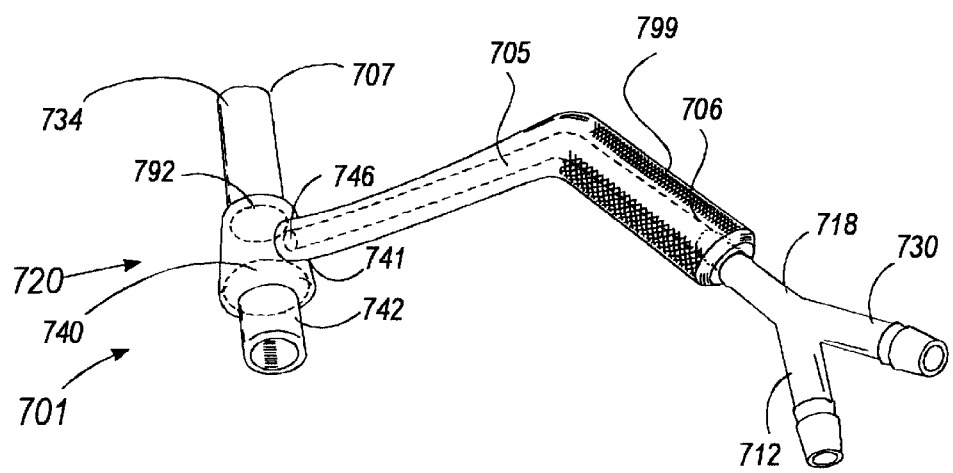
FIG. 12B is a side view of a manifold assembly and outer tubular member of FIG. 7 capable of receiving a second medical instrument or an inner tubular member and having an integral handle.

Referring now to FIGS. 11A, 11B and 13, the manifold portion 760 of the aortic catheter 701 has a manifold assembly 720 having a base 741 and a screw 742. The base is further comprised of a locking compression hemostasis valve 740 at its proximal end, a continuous communication channel 777 passing through the valve and the base 741 and a side port 746 that connects to the communication channel 777, distal to the hemostasis valve 740. The screw 742 has a male threaded distal end 748 and a through bore 779. Optionally, the screw can have a passive valve assembly 797 as illustrated in FIG. 11A. The screw 742 is configured to be coupled to a female threaded proximal end 798 of the base 741, and compress against the compression and locking hemostasis valve 740. The coupling relationship between the base 741 and the screw 742 is such that there is a fluid tight seal, configured for the transfer of fluid or a second shaft or medical instrument. Optionally, the manifold assembly 720 may have an integral or non-integral handle 799 as illustrated in FIGS. 12A and 12B. Illustrated in FIG. 12A is a non-integral handle 799 attached to the manifold assembly 720. The handle 799 may be removed from the manifold assembly at any time during the procedure and is configured to assist with the insertion of the catheter/introducer 701. Furthermore, in this illustrative embodiment the non-integral handle 799 and manifold assembly 720 may rotate about the outer tubular member 734 so that it does not interfere with the surgical procedure by using a dynamic seal 792. Alternatively, the handle 799 can be made of thousand series aluminum or other malleable material such that after the introducer is positioned, the handle 799 can be adjusted or bent so that it does not interfere with the surgical field. Illustrated in FIG. 12B is an integral handle 799 built into the manifold assembly 720. In this illustrative embodiment, the handle is multi-functional to serve as a handle 799 and also as a lumen 708, which is in fluid communication with side port 746. Again, the handle 799 and manifold assembly 720 can rotate about the outer tubular member 734 and may also be malleable.

Referring to FIG. 8 which is a magnified lateral cross-section of the aortic catheter 701 taken along line 8—8, the catheter shaft 702 is at least in part, configured in a coaxial arrangement comprising a corporeal lumen 708, an arch lumen 705 and an actuating lumen 714, which in this illustrative embodiment is in the form of an inflation lumen. The inflation lumen may be located on the exterior of the inner tubular member 733 as depicted, or alternatively may reside on the interior of the inner tubular member 733. The coaxial configuration creates an annular space 705, which defines the arch lumen 705. Referring to FIGS. 7 and 13, the coaxial length 770 of the catheter shaft 702 terminates at a distal arch opening(s) 707 along the length of the catheter shaft 702. Although the termination position may vary, arch anatomy is of primary consideration and the distal arch opening(s) 707 should be positioned for optimal fluid flow. Furthermore, the distal arch opening(s) 707 may be comprised of the annular opening or multiple openings circumferentially located around the exterior of the outer tubular member 734.

Referring now to FIGS. 7 and 9, FIG. 9 is a magnified lateral cross section of the aortic catheter 701 taken along line 9—9 of FIG. 7. The corporeal lumen 708 and the actuating lumen 714 continue to form the distal non-coaxial length 780 of the catheter shaft 702.

Referring now to FIGS. 7 and 10, FIG. 7 illustrates a magnified lateral cross section of the aortic catheter 701 taken along line 10—10 in FIG. 7. The corporeal lumen 708 continues through the catheter shaft 702 and terminates at a distal corporeal opening(s) 710 residing in the exterior of the distal tip 716.

Referring collectively to FIGS. 7 through 10, the inner tubular member 733 has an internal diameter preferably between 0.025" and 0.300", more preferably between 0.100" and 0.225", most preferably between 0.140" and 0.185". The outer tubular member 734 has an internal diameter preferably between 0.150" and 0.350", more preferably between 0.200" and 0.325", most preferably between 0.225" and 0.300".

The flow rate through the arch lumen 705 is preferably between 0.100 L/min and 3.00 L/min with a pressure drop between 0 mm Hg and 300 mm Hg, more preferably the flow rate is between 0.250 L/min and 2.50 L/min with a pressure drop between 0 mm Hg and 280 mm Hg, most preferably the flow rate is between 1.00 L/min and 2.00 L/min with a pressure drop between 0 mm Hg and 250 mm Hg when perfusing fluid therethrough.

The flow rate through the corporeal lumen 708 is preferably between 0.50 L/min and 8.00 L/min with a pressure drop between 0 mm Hg and 300 mm Hg, more preferably the flow rate is between 2.00 L/min and 6.00 L/min with a pressure drop between 0 mm Hg and 280 mm Hg, most preferably the flow rate is between 3.00 L/min and 5.00 L/min with a pressure drop between 0 mm Hg and 250 mm Hg.

The combined flow rate of the arch lumen 705 and corporeal lumen 708 is preferably between 0.50 L/min and 10.00 L/min with a pressure drop between 0 mm Hg and 300 mm Hg, more preferably the flow rate is between 1.00 L/min and 9.00 L/min with a pressure drop between 0 mm Hg and 280 mm Hg, most preferably the flow rate is between 2.00 L/min and 8.00 L/min with a pressure drop between 0 mm Hg and 250 mm Hg.

Referring back to FIGS. 7 and 13, the manifold portion 760 of the aortic catheter 701 has fittings for each of the catheter lumens. The arch lumen 705 has a proximal arch opening 706 connected to a Y-fitting 718. The Y-fitting 718 has an arch barb connector 730 or other suitable connector capable of being coupled to a CPB machine and a suction barb connector 712, or other suitable fitting capable of being coupled to a suction source. The corporeal lumen 708 has a proximal corporeal opening 709 coupled to a barb connector 717 or other suitable fitting capable of being coupled to a CPB machine. An actuating lumen 714, in this exemplary embodiment in the form of an inflation lumen, has a pressure monitoring balloon 745, or other suitable pressure monitoring device, and a proximal opening 732 connected to a stopcock 737, or other suitable fitting capable of being coupled to an inflation source.

An occlusion member 703, in this particular embodiment taking the form of an inflatable balloon, is in fluid communication with the actuating lumen 714, in the illustrative embodiment in the form of an inflation lumen, which extends from a proximal actuating opening 732 through a pressure monitoring balloon, or other pressure monitoring system or pressure regulating system 745 through the catheter shaft 702 to a distal actuating port 722 residing inside the interior of the occluding member 703. The occlusion member 703 has an inflated state 703' that is sized and configured to enable complete occlusion of the aorta, however engagement with the vessel wall may not be necessary to accomplish desired results. For example, partial inflation of the occlusion member 703 can effectively regulate fluid flow in the aorta enabling differential flow and pressure to the segmented regions of the aorta. Nevertheless, when engagement with the vessel wall does occur or is necessary it is non-traumatic. The occlusion member 703 is attached to the inner tubular member 733 by any number of known methods such as heat bonding welding, adhesive bonding or ultraviolet activated adhesive. Suitable materials for the occlusion member 703 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. Manufacturing techniques for making the balloons may be done by extruding, dipping and or blow molding.

The occlusion member 703 has a deflated state, in which the diameter is preferably not much larger than the diameter of the inner tubular member 733, and an inflated state 703', in which the occlusion member 703 is expandable to a diameter sufficient to occlude blood flow in the aorta. For use in adult human patients, the occlusion member 703 preferably has potential inflated outer diameter of approximately 1.0 cm to 8.0 cm. For pediatric patients or smaller patients the occlusion member 703 may be sized and configured to be smaller preferably 0.5 cm to 4.0 cm.

The arch lumen 705 extends from a proximal arch port 706 to a distal arch opening 707 proximal to the occlusion member 703. The arch lumen 705 may either serve as an arch perfusion lumen or a suction lumen depending upon the desired function during the cardiac procedure. For instance, suction in the arch may be desirable when embolic events are likely to occur. Furthermore, the aortic catheter of the present system may be used in conjunction with a venous cannula/catheter for retrograde perfusion of the brain wherein the arch lumen would serve as a venous return and the venous cannula would serve as the delivery instrument for oxygenated fluid to the brain in a retrograde direction.

When suction is desired the suction source draws fluid out of the aorta through the distal arch opening 707 through the arch lumen 705 to a cardiotomy reservoir which is in fluid communication with the suction barb connector 712. When arch perfusion is desirable, a multihead CPB machine coupled to the arch barb connector 730 delivers oxygenated fluid to the arch lumen 705 and out the distal arch opening 707. A manual, hydraulic, mechanical or a computerized switch enables the alternating function of the lumen by closing one lumen off and opening a fluid pathway for the other. The switch may be operated by using hemostats or tube pinchers, or may be as elaborate as using a solenoid or CPU connected to a Doppler machine that determines when embolic events are occurring and makes the switch electronically in connection with a mechanical operating assembly. Alternatively, a foot pedal may activate the switch.

The corporeal lumen 708 extends from the proximal corporeal opening 709 through the catheter shaft 702 to at least one distal corporeal opening 710 distal to the occlusion member 703. The distal corporeal opening may take the form of a single corporeal opening residing in the exterior of the catheter shaft 102 multiple openings or a single opening with a diffuser capable of reducing the "sandblasting effect".

The aortic catheter 701 may be coated with lubricious coatings that aid in the insertion and removal of the catheter as well as aid in hemocompatibility and anticoagualtion, the coatings are nonreactive and hydrophilic or hydrophobic. Medicated coatings may also be incorporated which are antithrombogenic, antimicrobial, anticancer, antigrowth factor, growth factor or anti-inflamatory. Examples of such coating are SLIP-COAT and MEDI-COAT made by STS Polymers Henrietta, N.Y. In addition, the shaft may be coated with echogenic material such as ECHO-COAT also made by STS Polymers Henrietta, N.Y. to aid in tracking and placement of the device with the use of ultrasound.

Furthermore, radiopaque markers and/or sonoreflective markers may be used to enhance imaging of the aortic catheter 701 using fluoroscopy or ultrasound, such as transesophageal echocardiography (TEE). Alternatively, or in addition thereto, the catheter can be configured to have magnets imbedded or placed on the catheter shaft 702 such that a sensing means detects the location of the catheter shaft 702 by sensing the static magnetic field strength gradient produced by the magnet associated with the catheter shaft 702. Furthermore a separate lumen may be provided for insertion of an optical fiber which is configured to emit visible light, ultraviolet light, near infrared light or infrared light. In this illustrative embodiment, the aortic catheter 701 includes a distal radiopaque marker 721 positioned within the occlusion member 703. The radiopaque marker may be made of a ring of dense radiopaque metal, such as gold, platinum, tantalum, tungsten or alloys thereof, or a ring of a polymer or adhesive material heavily loaded with a radiopaque filler material.

The catheter shaft 702 has a distal tip 716 made from any number of known materials such as polymers and elastomers, which include, but are not limited to, polyvinylchloride, polyurethane, polyethylene, polypropylene, polyamides (nylons), polyesters, latex, silicone, and alloys, copolymers and reinforced composites thereof. However, in a preferred embodiment the tip is made of a temperature sensitive polyurethane such as TECOFLEX or TECOPHILIC so that when the tip is exposed to a colder environment, the material becomes more rigid and is easily insertable into the ascending aorta while having the ability to become more pliable when exposed to the warmer temperature of body fluids. A method of achieving the desired results is to place the distal tip 716 in a 4-degree saline solution preoperatively. Furthermore, the distal tip 716 may be configured to have multiple corporeal flow ports 710 to reduce "jetting" when oxygenated blood is infused through the corporeal perfusion lumen 708.

The aortic catheter 701 further includes depth markers 724 that help determine the depth of the catheter shaft 702 inside the patient's anatomy. When the appropriate depth has been confirmed, through utilization of depth markers 724 or any other means suggested herein, the suture ring 725 can be adjusted to seat against the exterior of the tissue in order to better seal and keep the catheter shaft 702 in place during the surgical procedure.

Figure 15:
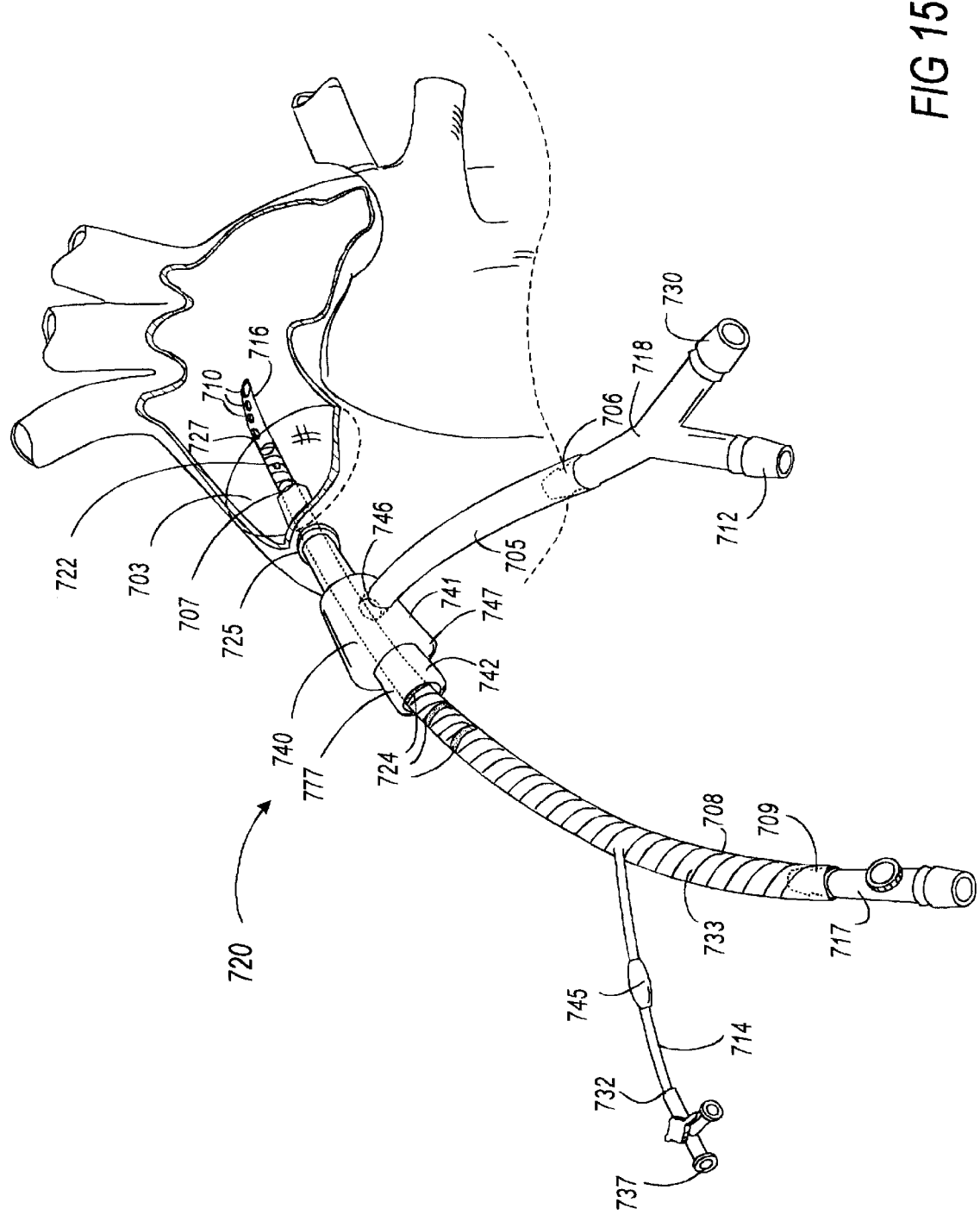
FIG. 15 is an in situ illustration of an embodiment of the present invention with part of the aorta cut away for illustrating placement of the aortic catheter.
Figure 16:
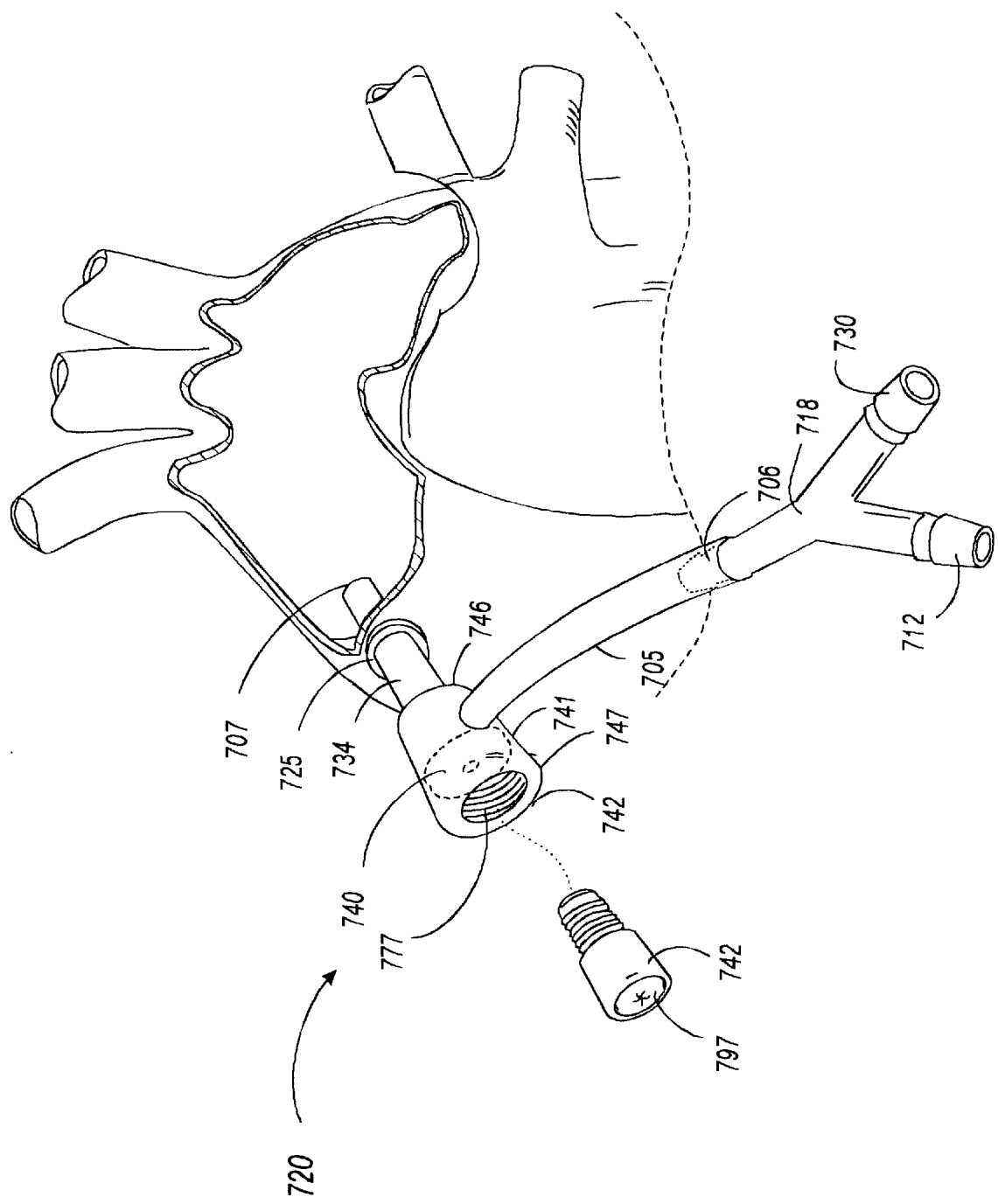
FIG. 16 an in situ illustration of the manifold assembly of FIG. 11A being used as an introducer cannula.

FIGS. 14, 15 and 16 illustrate the aortic catheter of FIG. 7 deployed in a patient's aorta configured for antegrade deployment and capable of differential perfusion and suction. The aortic catheter has an inner tubular member 733, in this illustrative embodiment in the form of a coil or braided reinforced shaft, which is configured to be completely or partially removed from the manifold assembly 720 and outer tubular member 734 or can be configured to have integral components that operate in a slidable relationship but not completely removable.

One method of using the catheter of the present invention is to access the patient's ascending aorta through a thorascopic access port, median sternotomy, rib-sparing minithoracotomy, thoracotomy with removal of ribs or costal cartilages, transverse sternotomy, or L-shaped, C-shaped and Z-shaped partial stemotomies. Then a purse string suture is performed in the wall of the ascending aorta that is followed by an aortic incision inside the purse string. The aortic catheter 701 is preoperatively prepared such that the inner tubular member 733 is already coaxially positioned through the manifold assembly 720 and is extending distally beyond the coaxial portion of the catheter shaft 702. The distal tip 716 of the inner tubular member 733 has been preoperatively primed in a 4 degree Fahrenheit environment to make it more rigid and is then introduced through the aortotomy incision. The catheter shaft 702 is advanced gradually dilating the opening until the outer coaxial portion resides within the lumen of the vessel. Once the proper depth has been achieved the suture ring 725 is moved in a distal direction slidable along the outer shaft 734 until it rests on the outer surface of the vessel wall creating a seal as illustrated in FIG. 14.

Figure 21A:
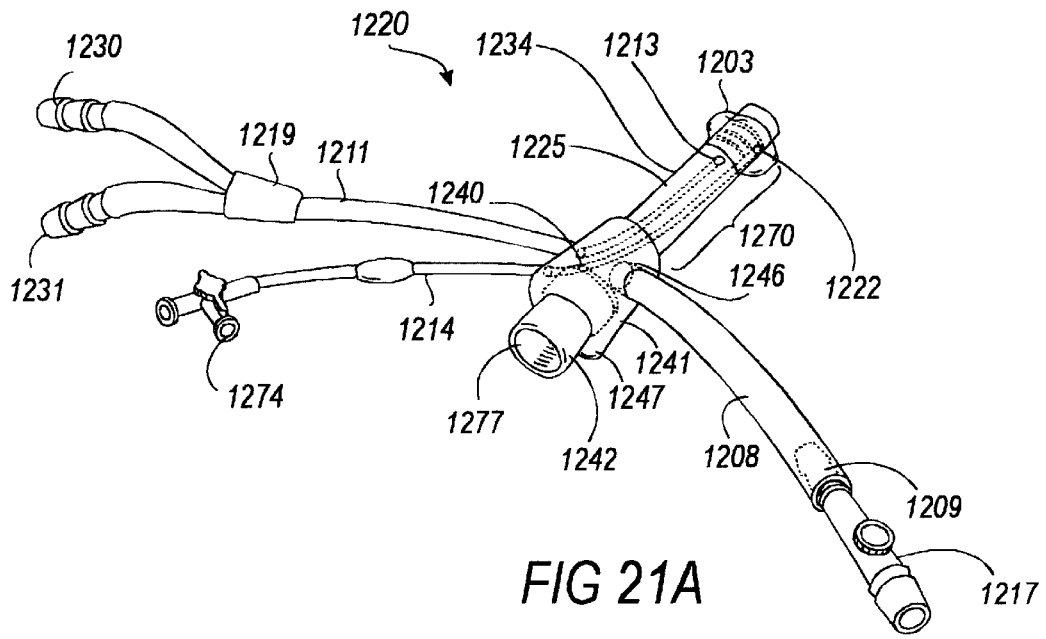
FIGS. 21A and 21B illustrate the aortic catheter of FIG. 17 with the inner tubular member completely removed from the outer tubular member and manifold assembly.

Alternatively, the inner tubular member 733 may be completely retracted from the manifold assembly 720 of the aortic catheter 701 as illustrated in FIGS. 11A and 11B. In this embodiment the outer member 734 and manifold assembly 720 are configured to serve as an introducer cannula. Referring to FIG. 16 the outer tubular member 734 is inserted through the aorta to the desired depth. Thereafter, the suture ring 725 is adjusted into place while the hemostasis valve 740 and screw 742 keep a fluid tight seal in the communication channel 777. Optionally, an occlusion member can also be attached to the outer tubular member 734 as illustrated in FIG. 21A. After the outer tubular member 734 has been properly secured, and the screw 742 adjusted, the inner tubular member 733 is inserted through the communication channel 777 and hemostasis valve 740 as illustrated in FIGS. 14 and 15. Optionally, the passive valve assembly 797 may be used.

Another method of using the outer tubular member 734 and manifold assembly 720 is for facilitating the use of other medical instruments by placing them through the communication channel 777 as procedural necessity dictates. For example, shunts as described in commonly owned, copending patent application Ser. No. 09/212,580, filed Dec. 1, 1998, and fluid separation devices as described in commonly owned, copending patent application Ser. No. 60/116,836 filed Jan. 22, 1999, which are hereby incorporated by reference in there entirety. Furthermore, angioplasty balloons, stents, atherectomy or ablation devices, stent removal devices, in stent restenosis devices, angiogenesis delivery devices, transmyocardial revasularization devices, valvuloplasty, electrophysiology devices, or optical and imaging devices may be inserted through the outer tubular member 734. Alternatively, the distal tip 716 may be made of a different material than catheter shaft 702. For example, the distal tip 716, the distal region of the catheter shaft 1102 or the majority of the catheter shaft, may be made of a temperature sensitive polyurethane such as TECOFLEX or TECOPHILIC such that when the tip is exposed to a colder environment, the material becomes more rigid and is easily insertable into the ascending aorta while having the ability to become more pliable when exposed to the warmer temperature of body fluids. One method of achieving the desired results is to place the distal tip 716 in a 4-degree saline solution preoperatively to rigidify the tip, then inserting the catheter 701 through the aortic wall. Once in the warmer of the aortic lumen, the distal tip softens due to the material composition and temperature sensitivity. Furthermore, the distal tip 716 may have multiple distal corporeal openings 710 to reduce fluid velocity through the distal corporeal openings 710. Alternatively, the distal tip may have a distal corporeal opening with a diffuser to reduce the "sandblasting" effect on the aortic wall.

Prior to aortic cannulation, or simultaneously thereto, one or more venous cannulae are introduced into the vena cava by way of bicaval, single atrial or cavoatrial approaches. Alternatively, venous cannulation of the femoral vein or the jugular vein may be used.

After the ascending aorta is accessed through any of the above listed techniques, and the venous cannula is in place, the inner tubular member 733 is navigated transluminally through the ascending aorta and across the aortic arch by using sensing means to determine the static magnetic field strength gradient produced by a magnet associated with the catheter shaft 702 under fluoroscopic or ultrasonic guidance, or under direct visualization with the aid of depth markers 724 or TEE. The inner tubular member 733 is advanced until the occlusion member 703, in this illustrative embodiment in the form of an occlusion balloon, is positioned in the descending aorta downstream of the left subclavian artery. When proper position is established, the occlusion member 703 is inflated as illustrated in FIG. 14. Using a multihead cardiopulmonary bypass pump or the like, differential perfusion is instituted. Normothermic (37 to 36 degrees C.) to tepid (36 to 32 degrees C.) oxygenated blood is perfused through the distal corporeal opening 710 downstream of the occlusion member 703 at a fluid flow rate ranging from 0.25 L/min to 7 L/min. Hypothermic (32 to 28 degrees C.) oxygenated blood is perfused through the distal arch opening 707 upstream of the occlusion member 703 at a fluid flow rate range from 0.15 L/min to 2.5 L/min. Hypothermic perfusion of the arch is continued and temperature is further reduced to profound hypothermia (18 to 12 degrees C.) until the heart begins to fibrillate inducing hypothermic arrest. A 5 meq bolus of KCl can be administered to completely arrest the heart if necessary and fluid flow to the heart and brain is reduced as a result of decreased metabolic consumption. Alternatively, or in addition thereto, a traditional external cross clamp may be used to occlude the ascending aorta upstream of aortic cannulation and cardioplegia is delivered through a separate cardioplegia needle, separate catheter or through a retrograde coronary sinus catheter to arrest the heart in the more traditional manner. Alternatively, after the outer tubular member has been inserted and locked into the appropriate position the inner tubular member is inserted therethrough. The occlusion member is positioned upstream of the brachiocephalic artery and inflated as Illustrated in FIG. 15. After inflation cardioplegia can be delivered in any manner previously described to arrest the heart. After the heart is arrested, the balloon is deflated and navigated transluminally to the descending aorta to create compartmentalization of the aorta as illustrated in FIG. 14. Cold blood perfusion keeps the heart in an arrested state and normothermic blood is delivered to the corporeal body.

Perfusion temperatures, perfusate compositions and flow rates can be optimized to each of the segmented regions of the patient's circulation for optimal organ preservation while on cardiopulmonary bypass. During the surgical procedure when embolic events are most likely to occur, a suction switch is activated, temporarily switching the arch lumen 705 from a perfusion source to a suction source enabling the withdrawal of fluid and embolic debris from the region upstream of the first occlusion member 703 through the distal suction opening 707 either manually or through sensing means such as Doppler. At the completion of the surgical procedure, the occlusion member 704 is deflated and normothermic blood is gradually introduced into the myocardium, whereupon the heart will spontaneously resume normal sinus rhythm as the heart rewarms. Alternatively, the occlusion member 703 may be deflated and the inner tubular member 733 repositioned in a retrograde direction distal to the distal arch opening 707 such that the occlusion member 703 resides in the ascending aorta between the coronary arteries and the brachiocephalic artery where reinflation of the occlusion member 703 may be done as is illustrated in FIG. 15. After reinflation of the occlusion member 703 preventing downstream flow of embolic fluid, gentle left ventricle compression is performed in conjunction with suction through the distal arch opening 707 to remove embolic debris before the heart is allowed to restart. Optionally, retrograde fluid may be delivered to the heart through a retrograde coronary sinus catheter to direct embolic fluid out of the myocardium and into the suction lumen 708 of the catheter 701. Perfusion to the brain is kept tepid to hypothermic to maintain the protective properties of cold blood perfusion to the brain and reducing fluid flow to the brain. After left ventricle compression and suction to clear the aortic lumen of potential embolic material, the occlusion member 703 is deflated and normothermic blood is gradually introduced into the myocardium, whereupon the heart will spontaneously resume normal sinus rhythm. If necessary, cardioversion or defibrillation may be applied to restart the heart. The patient is then weaned off bypass and the aortic catheter 701 and any other cannulae are withdrawn.

Figure 17:
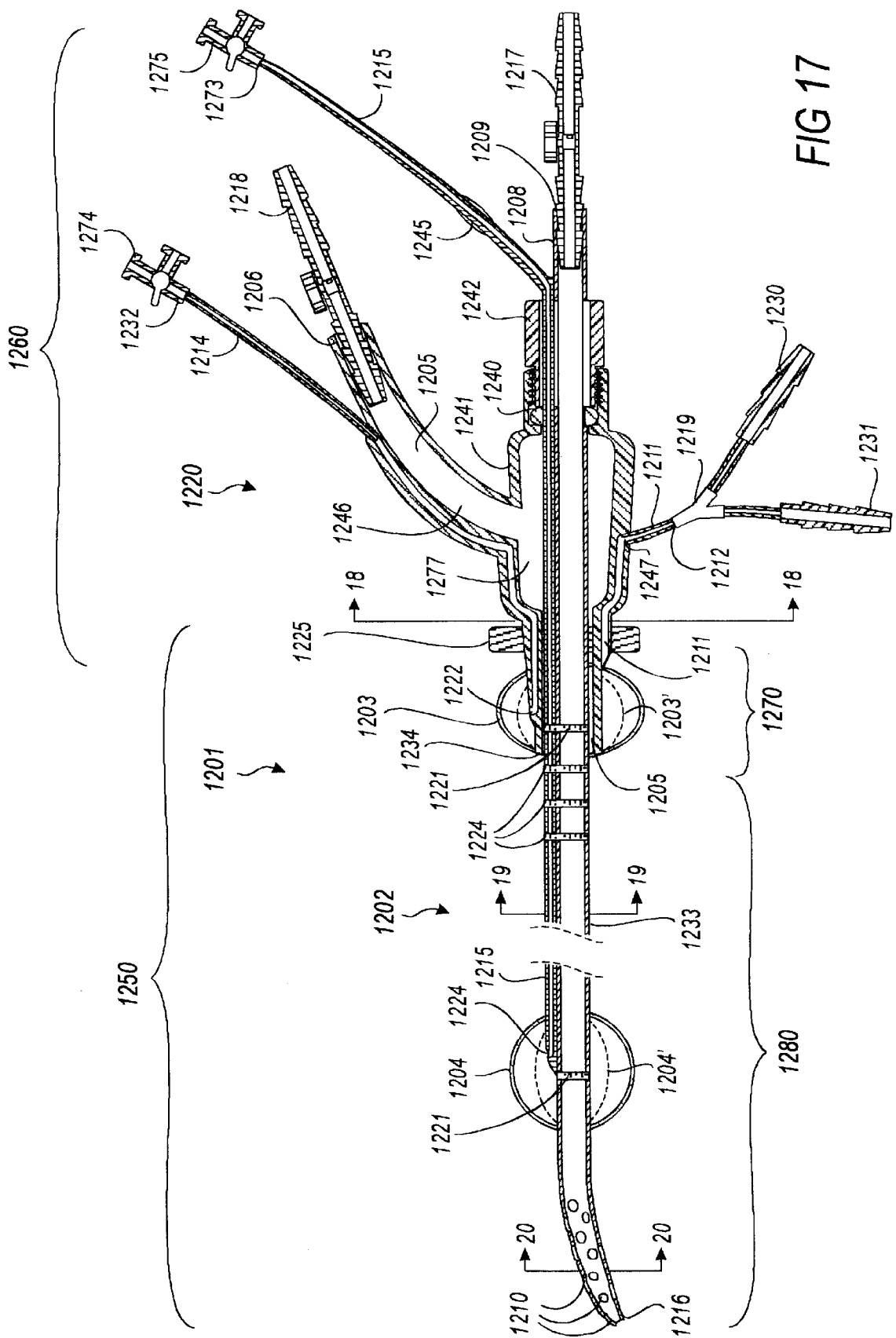
FIG. 17 illustrates a longitudinal cross-section of the aortic catheter of the present invention configured for antegrade deployment and capable of differential perfusion, aspiration and slidable movement of the inner tubular member.
Figure 20:
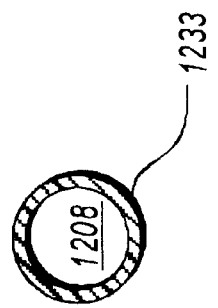
FIG. 20 is a magnified lateral cross-section of the aortic catheter of FIG. 17 taken along line 20—20 of FIG. 20.
Figure 19:
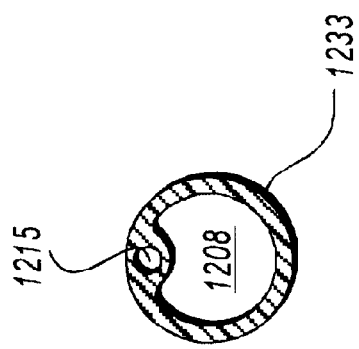
FIG. 19 is a magnified lateral cross-section of the aortic catheter of FIG. 17 taken along line 19—19 of FIG 17.
Figure 18:
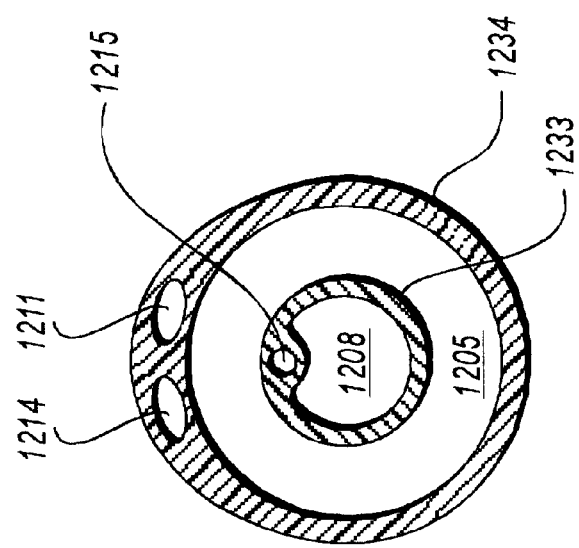
FIG. 18 is a magnified lateral cross-section of the aortic catheter of FIG. 17 taken along line 18—18 of FIG. 17 illustrating the coaxial configuration of the inner tubular member and outer tubular member.

FIGS. 17 through 20 illustrate another embodiment of an aortic catheter 1201 of the present invention configured for antegrade deployment and adapted to enable suction and differential perfusion. FIG. 17 is a longitudinal cross section of the aortic catheter 1201. FIG. 18 is a magnified lateral cross section of the aortic catheter 1201 taken along the line 18—18 in FIG. 17. FIG. 19 is a magnified lateral cross section of the aortic catheter 1201 taken along the line 19—19 in FIG. 17. FIG. 20 is a magnified lateral cross section of the aortic catheter 1201 taken along the line 20—20 in FIG. 20.

Referring to FIG. 17 the manifold portion 1260 of the aortic catheter 1201 has a manifold assembly 1220 having a base 1241 and a screw 1242. The base 1241 is further comprised of a locking compression hemostasis valve 1240 at its proximal end, a continuous communication channel 1277 passing through the valve 1240 and the base 1241, a first side port 1246 that connects to the communication channel 1277, distal to the hemostasis valve 1240 and a second side port 1247. The screw 1242 has a male threaded distal end and a through bore 1279. The screw 1242 is configured to be coupled to a female threaded proximal end of the base 1241, and compress against the compression and locking hemostasis valve 1240. The coupling relationship between the base 1241 and the screw 1242 is such that there is a fluid tight seal configured for the transfer of fluid or a second shaft or instrument. Optionally, the manifold assembly 1220 may have an integral or non-integral handle as illustrated in FIGS. 12A and 12B.

The shaft portion 1250 is comprised of a catheter shaft 1202 having an outer tubular member 1234 and an inner tubular member 1233 slidably disposed within the outer tubular member 1234, creating coaxial length 1270 and the non-coaxial length 1280. The coaxial configuration allows for the inner tubular member 1233 to be slidable relative to the communication channel 1277 and the outer tubular member 1234. The tubular members 1233 and 1234 may be made from any suitable material including, but not limited to, PEBAX, PVC, PET, polystyrene, polyvinylchloride, polyurethane, polyethylene, polypropylene, polyamides (nylons), polyesters, silicone, latex, stainless steel, platinum, titanium, nitinol, and alloys, copolymers and combinations thereof, as well as braided, coiled or counterwound wire or filament reinforced composites. The outer tubular member 1234 may be made of the same materials, as the inner as the inner tubular member 1233, may be coil reinforced, or may be made from other polymers such as polycarbonate, polysulfone or polyetherimide as well as steel, alloys or combinations thereof.

Figure 21B:
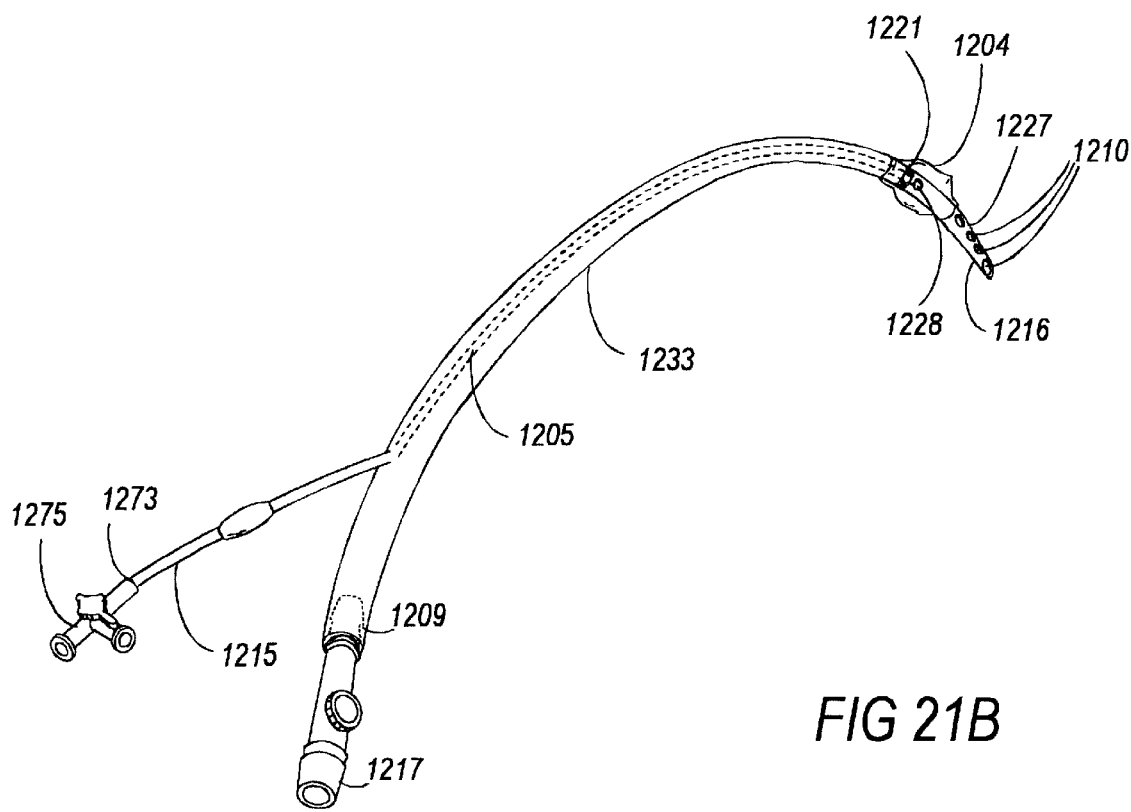

The non-coaxial portion 1280 has a curvature configured to reflect the patient's aortic anatomy as illustrated in FIG. 21B. The catheter shaft 1202 is of sufficient length to reach from an arterial insertion point to a patient's descending aorta. With the aforementioned requirements in mind the catheter shaft is preferably between 2 and 30 cm, more preferably between 7 and 20 cm, most preferably between 12 and 15 cm. Adjustments in the length of the catheter shaft are easily altered due to the coaxial sliding arrangement of the inner tubular member 1233 and the outer tubular member 1234.

FIG. 18 is a magnified lateral cross-section of the aortic catheter 1201 taken along line 18—18 in FIG. 17. The catheter shaft 1202 is at least in part, configured in a coaxial arrangement and is further comprised of a corporeal lumen 1208, an arch lumen 1205 a first actuating lumen 1214, a second actuating lumen 1215, and a suction/cardioplegia lumen 1211. The coaxial configuration creates an annular space 1205, which defines the arch lumen 1205. Referring to FIG. 17, the coaxial length 1270 of the catheter shaft 1202 terminates as one or more distal arch opening(s) 1207 along the length of the catheter shaft 1202. The distal arch opening may comprise a single annular opening or may have multiple external openings in the exterior of the outer tubular member 1234. Although the termination position may vary, arch anatomy is of primary consideration and the distal arch opening 1207 is intended to be in a position to enable optimal perfusion of flow and pressure to sustain the metabolic demands of the cerebral circulation. The suction/cardioplegia lumen 1211 terminates at a distal suction/cardioplegia opening 1213 along the length of the catheter shaft 1202 proximal to the first occlusion member 1203 on the exterior of the outer tubular member 1234. The first actuating lumen 1214, in this illustrative embodiment in the form of an inflation lumen, terminates at a first distal inflation port 1222 residing in the interior of the first occlusion member 1203. For clarity of illustration, the inflation lumen 1214 extends next to the arch lumen 1205, however the lumen arrangements may be located anywhere on the aortic catheter 1201 and may be designed in any way which enables the multipurpose functions of the aortic catheter. The second actuating lumen 1215, also in the form of an inflation lumen, terminates at a second distal inflation port 1228 residing in the interior of the second occlusion member 1204. FIG. 20 illustrates a magnified lateral cross section of the aortic catheter 1201 taken along line 20—20 in FIG. 17. The corporeal lumen 1208 defined by the internal diameter of the inner tubular member 1233 continues to form the distal non-coaxial length 1280 of the catheter shaft 1202 having at least one distal corporeal opening(s) 1210. The distal corporeal opening 1210 may take the form of a single opening, a single opening with a blood diffuser, or multiple openings of varying sizes and shapes. The distal corporeal opening may be in the form of a single opening or in the form of multiple openings residing in the exterior of the inner tubular member 1233.

Referring now to FIGS. 17 and 19, FIG. 19 illustrates a magnified lateral cross section of the aortic catheter 1201 taken along line 19—19 in FIG. 12. The corporeal lumen 1208 and second inflation lumen 1215 continue distally through the catheter shaft 1202. The second inflation lumen terminates at a second distal inflation port 1224 residing in the interior if the second occlusion member 1204.

Referring collectively to FIGS. 17 through 20, the inner tubular member 1233 has an internal diameter preferably between 0.025" and 0.300", more preferably between 0.100" and 0.225", most preferably between 0.140" and 0.185". The outer tubular member 1234 has an internal diameter preferably between 0.150" and 0.350", more preferably between 0.200" and 0.325", most preferably between 0.225" and 0.300".

The flow rate through the arch lumen 1205 is preferably between 0.100 L/min and 3.00 L/min with a pressure drop between 0 mm Hg and 300 mm Hg, more preferably the flow rate is between 0.250 L/min and 2.50 L/min with a pressure drop between 0 mm Hg and 280 mm Hg, most preferably the flow rate is between 1.00 L/min and 2.00 L/min with a pressure drop between 0 mm Hg and 250 mm Hg.

The flow rate through the corporeal lumen 1208 is preferably between 0.50 L/min and 8.00 L/min with a pressure drop between 0 mm Hg and 300 mm Hg, more preferably the flow rate is between 2.00 L/min and 6.00 L/min with a pressure drop between 0 mm Hg and 280 mm Hg, most preferably the flow rate is between 3.00 L/min and 5.00 L/min with a pressure drop between 0 mm Hg and 250 mm Hg.

The combined flow rate of the arch 1205 and corporeal 1208 lumens is preferably between 0.50 L/min and 10.00

L/min with a pressure drop between 0 mm Hg and 300 mm Hg, more preferably the flow rate is between 1.00 L/min and 9.00 L/min with a pressure drop between 0 nm Hg and 280 mm Hg, most preferably the flow rate is between 2.00 L/min and 8.00 L/min with a pressure drop between 0 mm Hg and 250 mm Hg.

Referring again to FIG. 17, the manifold portion 1260 of the aortic catheter 1201 has fittings for each of the catheter lumens. The arch lumen 1205 has a proximal arch opening 1206 connected to an arch barb connector 1218 or other suitable connector capable of being coupled to a CPB machine. The corporeal lumen 1208 has a proximal corporeal opening 1209 coupled to a barb connector 1217 or any other suitable fitting capable of being coupled to a CPB machine. The suction/cardioplegia lumen 1211 has a proximal opening 1212 connected to a Y-fitting 1219 having a cardioplegia connector 1230 or other suitable connector capable of being coupled to a cardioplegia source and a suction barb connector 1231, or other suitable fitting capable of being coupled to a suction source. A first actuating lumen 1214, in this exemplary embodiment in the form of an inflation lumen has a proximal opening 1232 connected to a stopcock 1274, or other suitable fitting capable of being coupled to an inflation source. A second actuating lumen 1215, in this exemplary embodiment in the form of an inflation lumen, has a pressure monitoring balloon 1245, or other monitoring or regulating device and a proximal opening 1273 connected to a stopcock 1275, or other suitable fitting capable of being coupled to an inflation source.

A first occlusion member 1203, in this exemplary embodiment in the form of an occlusion balloon, is located on the outer tubular member 1234. The first occlusion member 1203 is designed and configured to have an uninflated state 1203' and an inflated state 1203. In the uninflated state the first occlusion member 1203 is particularly suited for easy of entry into a vessel. In the inflated state the first occlusion member 1203 is expanded from the outer tubular member 1234, and is capable of preventing all or substantially all blood flow in the ascending aorta. For use in adult human patients, the first occlusion member 1203 preferably has an inflated outer diameter of approximately 1.0 cm to 6.0 cm. For pediatric patients the balloon may be substantially smaller. Preferably, the first occlusion member 1203 has an inflated length that is not significantly longer than its inflated diameter, or, more preferably, is shorter than its inflated diameter. This shortened inflated profile allows the first occlusion member 1203 to be easily placed within the ascending aorta between the coronary arteries and the brachiocephalic artery without any danger of inadvertently occluding either.

A second occlusion member 1204 is positioned distal to the first occlusion member 1203 and is separated at a distance preferably between 3 and 20 cm, more preferably between 8 and 15 cm. The distance is adjustable such that when the first occlusion member 1203 is positioned within the ascending aorta between the coronary arteries and the brachiocephalic artery, the second occlusion member 1204 will be positioned in the descending aorta downstream of the left subclavian artery. The second occlusion member 1204 may be more elongate, shorter or the same size as the first occlusion member 1203. The second occlusion member 1204 is designed and configured to have an uninflated state 1204' and an inflated state 1204. In the uninflated state 1204' the second occlusion member 1204 is particularly suited for easy of entry into a vessel. In the inflated state the second occlusion member 1203 is expanded from the outer tubular member 1234, and is capable of preventing all or substantially all blood flow in the descending aorta. In addition, the outer surface of the first and second occlusion members 1203 and 1204 may include a friction increasing coating or texture to increase friction with the aortic wall when deployed.

The aortic catheter 1201 may be coated with lubricious coatings that aid in the insertion and removal of the catheter as well as aid in hemocompatibility. The coatings are nonreactive and hydrophilic or hydrophobic. Furthermore, medicated coatings may also be incorporated which are antithrombogenic, antimicrobial, anticancer, antigrowth factor, growth factor or anti-inflamatory. Examples of such coating are SLIP-COAT and MEDI-COAT made by STS Polymers Henrietta, N.Y. In addition, the shaft may be coated with echogenic material such as ECHO-COAT also made by STS Polymers Henrietta, N.Y. to aid in tracking and placement of the device with the use of ultrasound.

The aortic catheter 1201 may include one or more markers, in the form of radiopaque markers and/or sonoreflective markers, to enhance imaging of the aortic catheter 1201 using fluoroscopy or ultrasound, such as transesophageal echocardiography (TEE).). Alternatively, or in addition thereto, the catheter can be configured to have magnets imbedded or placed on the catheter shaft 1202 such that a sensing means detects the location of the catheter shaft 1202 by sensing the static magnetic field strength gradient produced by the magnet associated with the catheter shaft 1202. In this illustrative embodiment; the aortic catheter 1201 includes radiopaque markers 1221 positioned within the occlusion members 1203 and 1204. The radiopaque marker may be made of a ring of dense radiopaque metal, such as gold, platinum, tantalum, tungsten or alloys thereof, or a ring of a polymer or adhesive material heavily loaded with a radiopaque filler material.

The distal tip 1216 is made from any number of known materials such as polymers and elastomers, which include, but are not limited to, polyvinylchloride, polyurethane, polyethylene, polypropylene, polyamides (nylons), polyesters, latex, silicone, and alloys, copolymers and reinforced composites thereof. However, in a preferred embodiment the tip is made of a temperature sensitive polyurethane such as TECOFLEX or TECOPHILIC so that when the tip is exposed to a colder environment, the material becomes more rigid and is easily insertable into the ascending aorta while having the ability to become more pliable when exposed to the warmer temperature of body fluids. Furthermore, the distal tip 1216 may be configured to have multiple corporeal flow ports, or single opening with a diffuser to reduce "jetting" when oxygenated blood is infused through the corporeal perfusion lumen 1208.

The aortic catheter 1201 further includes depth markers 1224 that help determine the depth of the catheter shaft 1202 inside the patient's anatomy. When the appropriate depth has been confirmed, the suture ring 1225 can be adjusted to seat against the exterior of the tissue in order to better seal and keep the catheter shaft 1202 in place during the surgical procedure.

FIG. 22 illustrates the aortic catheter 1201 of FIG. 17 deployed in a patient's aorta configured for antegrade deployment and capable of differential perfusion and suction. In many respects this embodiment of the aortic catheter 1201 is similar in materials, construction and dimensions as embodiments previously described. However, in this embodiment there are two occlusion members 1203 and 1204 and the manifold assembly with the outer tubular member 1234 may be used as an introducer as illustrated in FIG. 21A.

Figure 23:
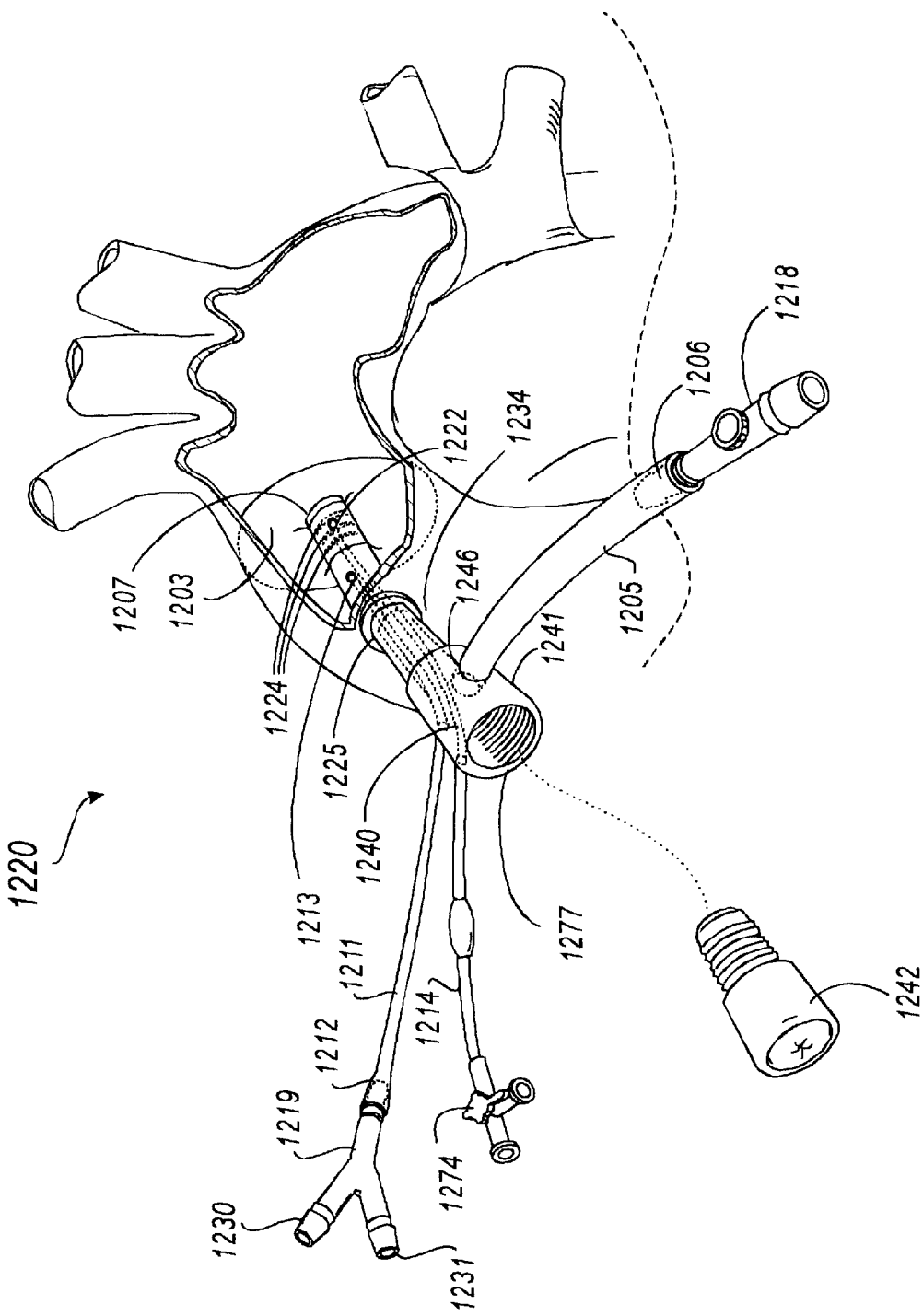
FIG. 23 is an in situ illustration of the aortic catheter of FIG. 17 with the manifold assembly being used as an introducer cannula or as a stand alone perfusion instrument with elimination of the external crossclamp.

One method of using the present invention is to access a patient's aorta through a median sternotomy, thorascopic access port, rib-sparing minithoracotomy, thoracotomy with removal of ribs or costal cartilages, transverse sternotomy, or L-shaped, C-shaped and Z-shaped partial sternotomies. Then performing a purse string suture in the wall of the ascending aorta followed by an aortic incision inside the purse string. The aortic catheter 1201 is preoperatively prepared such that the inner tubular member 1233 is already coaxially positioned through the manifold assembly 1220 and is extending distally beyond the outer tubular member 1234 of the catheter shaft 1202. The distal tip 1216 of the inner tubular member 1233 is then introduced through the aortotomy incision gradually dilating the opening until the outer coaxial portion resides within the lumen of the vessel as illustrated in FIG. 22. Alternatively, as shown in FIGS. 21A and 21B, the inner tubular member 1233 may be completely retracted from the manifold assembly 1220. The manifold assembly 1220 is now configured to serve as an introducer cannula, or as a stand alone perfusion cannula with an ascending aortic occlusion member 1203 eliminating the need for an external cross clamp as illustrated in FIG. 23. When used as an introducer the manifold assembly 1220 and outer tubular member 1234 are inserted through the aorta to the desired depth. After insertion of the outer tubular member 1234, the inner tubular member 1233 may be inserted through the communication channel 1277 and the locking hemostasis valve 1240 is compressed by screw 1242 creating a fluid tight seal and locking the inner tubular member 1233 in place. Furthermore, it is also contemplated that other medical instruments may also be placed through the manifold assembly 1220 as procedural necessity dictates. For example, shunts as described in commonly owned, copending patent application Ser. No. 09/212,580, filed Dec. 4, 1998, fluid separation devices as described in commonly owned, copending patent application Ser. No. 60/116,836 filed Jan. 22, 1999 which are hereby incorporated by reference in there entirety. Furthermore, other instruments may be inserted through the manifold assembly including; angioplasty balloons, stents, atherectomy or ablation devices, stent removal devices, in stent restenosis devices, angiogenesis delivery devices, transmyocardial revascularization devices, electrophysiology devices, or optical imaging and location devices may be inserted through the manifold assembly 1220 and outer tubular member 1234.

Alternatively, the aortic catheter 1201 may have a distal tip 1216 on the inner tubular member 1233 made from a temperature sensitive material such as TECOFLEX or TECOPHILIC wherein the aortic catheter 1201 may directly penetrate the vessel wall without the need for an aortotomy or introducer cannula when the aortic catheter is configured to have integral components. Alternatively, the inner tubular member 1233 may be pre-loaded within the outer tubular member 1234 but not extending beyond the outer tubular member 1234. Furthermore, the manifold assembly 1220 may have an integral or non-integral handle similar in function and design to FIGS. 12A and 12B.

Prior to aortic cannulation, or simultaneously, one or more standard venous cannula are introduced into the vena cava by way of bicaval, single atrial or cavoatrial approaches or alternatively, a balloon venous cannula may be introduced to selectively isolate drainage or perfusion of the inferior vena cava, superior vena cava and right atrium. Alternatively, venous cannulation of the femoral vein or the jugular vein may be used. For example one or more cannulae or catheters may have occlusion balloons mounted on the shaft, which are capable of segmenting the venous system. By implementing these alternative venous cannulation techniques it is also possible to perform retrograde perfusion to the brain through the venous catheter, using the arterial catheter 1201 to drain deoxygenated fluid through the distal arch opening 1207. A coronary sinus catheter may also be implemented to deliver retrograde cardioplegia to the myocardium while using the suction/cardioplegia lumen 1211 to drain the fluid to a cardioplegia reservoir or venous reservoir. In addition, alternating forms of retrograde/antegrade delivery would also be possible, giving the most versatile system possible.

After the ascending aorta is accessed through any of the above listed techniques, and the venous cannula is in place, the inner tubular member 1233 is navigated transluminally through the ascending aorta and across the aortic arch under fluoroscopic, ultrasound guidance, by the sensing of a static magnetic field strength gradient produced by a magnet located on or in the catheter shaft 102, or under direct visualization with the aid of depth markers 1224. The inner tubular member 1233 is advanced until the second occlusion member 1204, in this illustrative embodiment in the form of an occlusion balloon, is positioned in the descending aorta downstream of the left subclavian artery. When proper position is established, the first occlusion member 1203 is inflated. Using a multihead cardiopulmonary bypass pump or the like, differential perfusion is instituted. Normothermic (37 to 36 degrees C.) to tepid (36 to 32 degrees C.) oxygenated blood is perfused through the distal corporeal opening 1210 downstream of the second occlusion member 1204 at a fluid flow rate ranging from 1 L/min to 7 L/min. Hypothermic (32 to 28 degrees C.) oxygenated blood is perfused through the distal arch suction opening 1207 upstream of the second occlusion member 1204 at a fluid flow rate from 0.25 L/min to 1.5 L/min. Hypothermic perfusion of the arch is continued and the temperature is further reduced to profound hypothermia (18 to 12 degrees C.) until the heart begins to fibrillate. A 5 meq bolus of KCl can be administered to completely arrest the heart whereby and fluid flow to the heart and brain is reduced since metabolic rate is slowed and oxygen consumption is reduced.

Alternatively, the first occlusion member 1203 and the second occlusion member 1204 can both be inflated, creating a segmentation of the myocardium from the aortic arch and corporeal circulations. After perfusion begins, taking some of the pumping load off the heart, the first occlusion member 1203 is inflated and cardioplegia is delivered to the myocardium through the suction/cardioplegia lumen 1211 and out the distal suction/cardioplegia opening 1213. Alternatively, or in addition to the suction/cardioplegia lumen 1211, cardioplegia may be delivered through a separate cardioplegia needle, catheter or through a retrograde coronary sinus catheter to arrest the heart in the more traditional manner.

Perfusion temperatures, perfusate compositions and flow rates may be optimized to each of the segmented regions of the patient's circulation for optimal organ preservation while on cardiopulmonary bypass. The system of the present invention is configured for retrograde perfusion, as well as retrograde cardioplegia delivery, in addition to alternating forms of perfusion and cardioplegia delivery. During the surgical procedure when embolic events are most likely to occur, a suction switch is activated, switching the suction/cardioplegia lumen 1211 from a cardioplegia source to a suction source, enabling the withdrawal of fluid and embolic debris from the region upstream of the first occlusion member 1203 through the distal suction opening 1207. Furthermore, arch perfusion can be reversed and retrograde perfusion to the brain may be accomplished to divert emboli downstream. At the completion of the surgical procedure, the first and second occlusion members 1203 and 1204 are deflated and normothermic blood is gradually introduced into the myocardium, whereupon the heart will spontaneously resume normal sinus rhythm as the heart rewarms. If necessary, cardioversion or defibrillation may be applied to restart the heart. The patient is then weaned off bypass and the aortic catheter 1201 and any other cannulae are withdrawn.

FIG. 24 is a schematic diagram, illustrating the catheter system of the present invention capable of differential perfusion and suction. A venous cannula 1799 has a proximal fitting connected to tubing 1797, which is in fluid communication with venous reservoir 1796. The venous cannula 1799 is inserted into the right atrium or vena cava by bicaval, single atrial, cavoatrial or two-stage technique. Alternatively, a peripheral vein may be used as an insertion site used in conjunction with a single or double balloon venous catheter. Venous drainage is attained by creating negative pressure through either a controlled vacuum within the venous reservoir 1796, gravity, or using a pump to create negative pressure within the venous line resulting in blood being drawn into the venous reservoir 1796. In fluid communication with the venous reservoir 1796 is a centrifugal pump 1795 which draws blood from the venous reservoir 1796 through a combined heat exchanger/membrane oxygenator 1794 to the aortic catheter 1701. Alternatively, a bubble oxygenator can utilized, in which case, the bypass circuit arrangement changes slightly in that the bubble oxygenator is positioned proximal to the arterial pump 1795 and the venous reservoir 1796. In addition, the bubble oxygenator is positioned beyond the defoaming chambers and is usually part of an assembly that contains an integral heat exchanger.

A separate suction catheter 1793 is provided to aspirate blood from the surgical filed. The suction catheter 1793 has a proximal fitting connected to primary suction tubing 1792 in fluid communication with a suction source. Suction is established by using negative pressure to draw blood from the patient into a cardiotomy reservoir 1790, in this illustrative embodiment a roller pump 1791 is used. Alternatively suction can be established by using a centrifugal pump, wall suction, by applying constant vacuum or through gravity. From the cardiotomy reservoir 1790, the blood may be discarded or sent back into the venous reservoir 1796. Thereafter the blood is pumped to the aortic catheter 1701. The utilization of slow flow rates and large diameter suction tips has proven to be beneficial in helping to minimize blood trauma. In addition the surgical team can utilize centrifugal cell washers (cell saver) or an autotransfusion device to supplement the cardiotomy suction in order to remove extracardiac blood and cardioplegia and to maximize red blood cell recirculation into the extracorporeal circuit.

A vent catheter 1789 is provided for venting blood from the left ventricle. The vent catheter 1789 has a proximal fitting configured to be coupled to vent tubing 1788, which is in fluid communication with a roller pump 1787. Alternatively, gravity may be used as a siphoning means for removing blood from the left ventricle to help prohibit ventricular hypertrophy. During the surgical procedure the vent catheter 1789 is inserted at the junction of right superior pulmonary vein and left atrium and advanced across the mitral valve to the left ventricle. Alternatively, the vent catheter 1789 can be inserted directly through the apex of the left ventricle. Once the vent catheter 1789 is in proper position, blood is withdrawn from the left ventricle into the cardiotomy reservoir 1791.

An aortic catheter 1701 is provided to deliver oxygenated blood to the patient. Typically, before inserting the aortic catheter 1701 into the aorta, a purse string suture is placed on the anterior aortic wall proximate or upstream to the brachiocephalic artery. With the aorta stabilized a stab incision or aortotomy incision is placed within the purse string of sufficient size to enable the aortic catheter 1701 to be easily slipped into the aorta. Once inserted, the catheter shaft 1702 is navigated transluminally until a first occlusion member 1703 resides in the ascending aorta upstream of the brachiocephalic artery and a second occlusion member 1704 resides downstream of the left subclavian artery. Once proper position is established either through TEE or by referring to depth markers 1735, the "keeper" on the purse string is snugged down and the suture ring 1725 is positioned into place to create a seal against the exterior of the anterior aortic wall. The second occlusion member 1704, in this illustrative embodiment in the form of an inflatable occlusion balloon, is inflated with saline from a syringe and differential perfusion begins. Blood is perfused to the arch vessels and myocardium through the arch distal opening 1707 at a first temperature and the corporeal body is perfused through the distal corporeal opening 1710 at a second temperature or the same temperature. The myocardium also receives oxygenated blood from the distal arch opening 1707 until the myocardium reaches a predetermined temperature. The first occlusion member 1703 is inflated with saline from a syringe. Cold, warm or normothermic cardioplegia is initiated through the suction/cardioplegia distal opening 1713 to completely arrest the heart. Alternatively, a separate catheter, retrograde coronary sinus catheter or cardioplegia needle may deliver cardioplegia to arrest the heart. Once the heart is arrested or when the temperature is reduced sufficiently to reduce cellular metabolic demand of the heart and brain, the perfusion flow is reduced.

The aortic catheter 1701 has fittings attached to the proximal end of the catheter shaft 1702, which are coupled to connectors in fluid communication with the extracorporeal circuit. Blood is pumped from a venous reservoir 1796 to an integral heat exchanger membrane oxygenator 1794. After appropriate treatment the blood is then pumped through tubing 1801 which has a Y-split connected to tubing 1719 and 1720. Arch flow is separated into tubing 1719 and corporeal flow is separated into tubing 1720. The blood intended for the arch system is pumped through tubing 1719 to the arch lumen 1705 and out the distal arch opening(s) 1707, to provide life sustaining metabolic demands of the cerebral system. To provide adequate blood flow to the corporeal system, the blood is pumped from the same venous reservoir 1796 through the same integral heat exchanger membrane oxygenator 1794 as the arch. Blood is then pumped through the same Y-split, however a predetermined amount of flow is directed into a second heat exchanger 1721 which is in fluid communication with tubing 1720 and the corporeal lumen 1708. The corporeal lumen opens at a distal corporeal opening(s) 1710 for providing the life sustaining metabolic demands of the corporeal system. A switch 722 having a first position and a second position is in fluid communication with the suction/cardioplegia lumen 1711. The switch has a cardioplegia connector 1724 and a suction barb connector 1725. Connected to cardioplegia barb connector 1724 is tubing 1726 in fluid communication with cardioplegia source 1727 and roller pump 1748. Connected to suction barb connector 1725 is tubing 1728 in fluid communication with suction source 1791. Since aortic suction may not always be desirable the suction switch 1736 serves as a switching mechanism to occlude tubing 1728 when suction is not desirable. In addition, cardioplegia delivery is not always necessary, therefore the suction switch 1736 is positioned to occlude tubing 1726 when cardioplegia delivery is not necessary. Alternatively, other mechanical, hydraulic, or electrical switching mechanisms may be used to alternate between suction and cardioplegia. For example a foot pedal 1964 may activate the suction switch 1736 or the suction switch can be activated through an electronic signal in combination with embolic sensing means for example Doppler 1962 or through other remote activation means. The catheter system preferably includes in line arterial filters, bypass lines, flow meters, bubble detectors, and pressure monitoring devices which are typically included in extracorporeal circuits as is well known to one of ordinary skill in the art.

Figure 25:
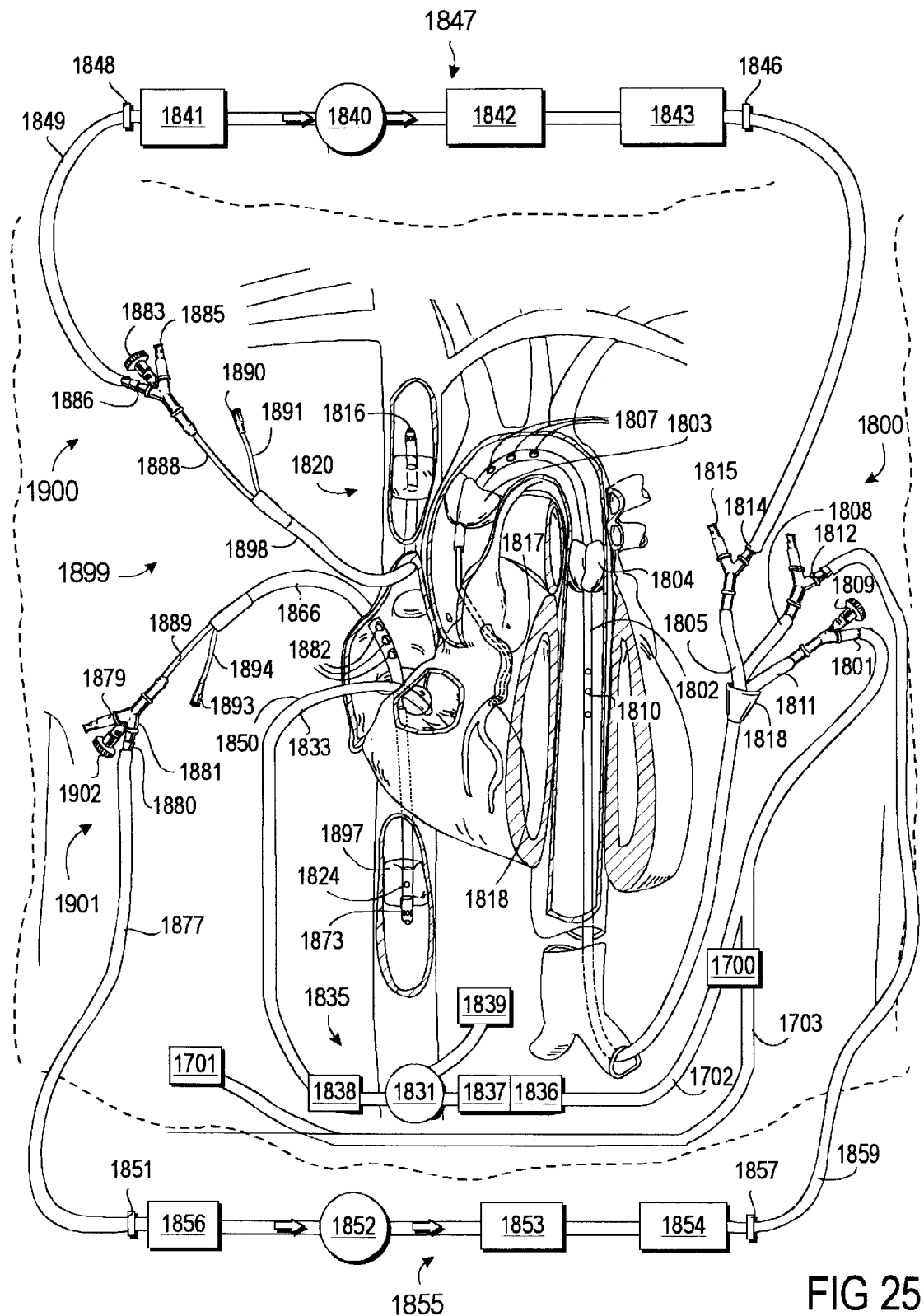
FIG. 25 is an in situ illustration of an embodiment of the present invention having an aortic catheter configured for supporting a therapeutic system and designed to accomplish differential perfusion with occluding members in the form of valves.

FIG. 25 illustrates the catheter system of the present invention configured for retrograde deployment via a peripheral artery. The catheter system, which may comprise one or more venous and arterial catheters, may be introduced peripherally or centrally for performing any surgical or therapeutic procedure. For example, the system of the present invention can support therapeutic interventions including but not limited to angioplasty balloons, stents, atherectomy or ablation devices, stent removal devices, in stent restenosis devices, angiogenesis delivery devices, transmyocardial revasularization devices, valvuloplasty, electrophysiology devices, gene therapy delivery devices or optical and imaging devices.

The catheter system is comprised of an aortic catheter 1800 configured to segment the aorta into various subsystems, a venous catheter system 1899 capable of segmenting the venous system into various subsystems, a coronary sinus catheter 1850 and a therapeutic catheter 1820. The present system is capable of complete isolation of the myocardial, cerebral and corporeal circulations for antegrade or retrograde perfusion to the cerebral circulation and antegrade, retrograde and/or alternating antegrade and retrograde cardioplegia delivery to the myocardium. Furthermore the present invention is capable of receiving a second therapeutic catheter, drug delivery catheter or fiberoptic catheter.

The aortic catheter 1800 in this illustrative embodiment has occlusion members 1803 and 1804 in the form of external valves. Catheter valves suitable for use as flow control members are described in commonly owned, copending U.S. Pat. Nos. 5,827,237 and 5,833,671 and commonly owned, copending patent application Ser. No. 08/665,635 filed Jun. 18, 1996 to Macoviak et al. which are hereby incorporated by reference in their entirety. Alternatively, occlusion balloons may be used instead of valves, in addition to valves, or in combination with valves.

The aortic catheter 1800 is configured for retrograde introduction into the patient's aorta via a peripheral arterial access point, such as the femoral artery. Alternatively, the aortic catheter may be configured for central approach without departing from the scope of the invention. The aortic catheter 1800 has a catheter shaft 1802 that includes an arch perfusion lumen 1805, a corporeal perfusion lumen 1808 and a fluid/instrument lumen 1811. A first occluding member 1803, in this illustrative embodiment in the form of a peripheral flow control valve is mounted on the tubular shaft 1802 so that it is positioned in the ascending aorta between the coronary arteries and the right brachiocephalic artery and a second occluding member 1804, also in the form of a peripheral flow control valve, is mounted on the tubular shaft 1802 so that it is positioned in the descending aorta downstream of the left subclavian artery. In one preferred embodiment, the first occluding member 1803 is an antegrade valve that allows greater fluid flow in the antegrade direction than in the retrograde direction, and the second occluding member 1804 is a retrograde valve that allows greater fluid flow in the retrograde direction than in the antegrade direction. The corporeal lumen 1808 extends through the tubular shaft 1802 from a corporeal perfusion fitting on the proximal end of the catheter 1800 to one or more corporeal perfusion ports 1810 on the catheter shaft 1802 proximal to second occlusion member 1804. The corporeal fitting has a barb connector 1812 or other suitable connector capable of being coupled to a CPB machine and a luer fitting or other suitable fitting capable of withdrawing fluids or injecting fluids. Alternatively, if the catheter is constructed without the corporeal perfusion lumen 1808, corporeal perfusion can be provided through a coaxial, collateral or contralateral perfusion cannula. The arch perfusion lumen 1805 extends through the catheter shaft 1802 from an arch perfusion fitting on the proximal end of the catheter to one or more arch perfusion ports 1807 on the catheter shaft 1802 between the first and second occlusion members 1803 and 1804 respectively. The arch perfusion fitting has an arch barb connector 1814 or other suitable connector configured for being coupled to a CPB machine and a luer fitting 1815 or other suitable fitting for withdrawing or injecting fluid. Optionally, arch pressure monitoring may be accomplished through a separate arch monitoring lumen or through a separate arch device lumen capable of receiving a monitoring assembly for flow, pressure and chemical composition. Alternatively, a pigtail vent catheter may be inserted through the lumen to vent the left ventricle. Furthermore, an optional aortic root monitoring lumen may be provided to accomplish substantially the same features as the arch monitoring lumen.

The fluid/instrument lumen 1811 extends through the tubular shaft 1802 from a fluid/instrument fitting on the proximal end of the catheter to a distal port 1816 on the tubular shaft distal to the first occlusion member 1803. The fluid/instrument fitting has a barb connector 1801 or other suitable fitting capable of being coupled to a suction/ cardioplegia source and a Touy-Borst fitting 1809 or other suitable fitting capable of receiving a second instrument. The fluid/instrument lumen 1811 is made with an internal diameter sufficient to accommodate a therapeutic, optical, imaging or pigtail venting catheter as well as provide adequate suction to the aortic root or alternatively cardioplegia delivery to the coronary arteries through the annular space created when a second instrument is in use or alternatively when no instrument is in use. Optionally, the aortic catheter 1800 may also include a root pressure lumen and an arch pressure lumen that extends through the tubular shaft from fittings on the proximal end of the catheter shaft 1802.

The therapeutic catheter in this illustrative embodiment is in the form of a stent therapeutic system 1820, including a stent catheter 1817, and a guidewire 1818. The fluid/ instrument lumen 1811 of the aortic catheter 1800 should be made with an internal diameter sufficient to accommodate the chosen catheter with additional clearance for annular perfusion or aspiration.

The venous catheter system 1899 may include one or more venous cannulae/catheters. In this illustrative embodiment the venous catheter system is comprised of an inferior vena cava catheter and a superior vena cava catheter. The superior vena cava catheter 1900 has a first occlusion balloon 1896 or other expandable occlusion member mounted on the tubular shaft 1898, which is positioned within the patient's superior vena cava when in the operative position, and a second venous catheter 1901 has a second occlusion balloon 1897 or other expandable occlusion member, mounted on the tubular shaft 1166, which is positioned within the patient's inferior vena cava when in the operative position. Optionally, the venous catheter system 1899 may be configured for femoral artery introduction on a single shaft. In these alternative embodiments the first occlusion balloon is mounted near the distal end of the tubular shaft and the second occlusion balloon is mounted somewhat proximal to the first. Alternatively, for jugular vein introduction on a single shaft, these positions are reversed.

A first balloon inflation lumen 1891, connected to fitting 1890, extends through the tubular shaft 1898 to a balloon inflation port 1823 within the first occlusion balloon 1896. In addition, a superior vena cava monitoring lumen may be implemented to monitor pressure, temperature, chemical composition and oxygen saturation in the superior vena cava. Optionally, oxygen saturation may be measured through a jugular bulb or thorough a cerebral oximeter. Optionally, a separate lumen may be provided for measuring pressure, temperature, oxygen saturation and chemical composition in the superior vena cava. The second balloon inflation lumen 1894, connected to fitting 1893, extends through the tubular shaft 1166 to a balloon inflation port 1824 within the second occlusion balloon 1897.

The superior vena cava catheter 1900 has a first venous drainage lumen 1888 extending through the tubular shaft 1898, to one or more superior vena cava drainage ports 1895 distal to the first occlusion balloon 1896. The inferior vena cava catheter has a second venous drainage lumen 1889 extending through the tubular shaft 1166, to one or more inferior vena cava drainage ports 1873 distal to the second occlusion balloon 1897.

The proximal ends of the venous drainage catheters have fittings for each of the catheter lumens. The first venous drainage lumen 1888, of the superior vena cava catheter 1900, is coupled to a three-way fitting having a barb connector 1886 for connection to an external CPB machine, a luer connector 1885 capable of monitoring superior vena cava pressure, temperature and chemical compositions and a Touhy-Borst adapter 1883 or other hemostasis valve on the proximal end of the catheter 1900 configured for receiving a separate monitoring device for measuring oxygen saturation or other chemical testing in the superior vena cava or for insertion of a guidewire. The second venous drainage lumen 1889, of the inferior vena cava catheter 1901, is coupled to a three-way fitting having a barb connector 1880, or other suitable fitting capable of being coupled to a CPB machine, a luer fitting 1879 capable of monitoring inferior vena cava pressure, temperature and chemical compositions and a Touhy-Borst adapter 1902 or other hemostasis valve on the proximal end of the catheter 1901 configured for receiving a separate monitoring device for measuring oxygen saturation or other chemical testing in the superior vena cava or for insertion of a guidewire.

The cerebral loop of the circulatory support system is created by having venous drainage ports 1895 in fluid communication with the superior vena cava drainage lumen 1888. Coupled to the superior vena cava drainage lumen 1888 is a barb connector 1886 coupled to tubing 1849 in fluid communication with inflow port 1848 of a first blood conditioning system 1847. The blood is conditioned and pumped through the outflow port 1846 of the first blood conditioning system 1847 to the arch perfusion lumen 1805 of the arterial cannula 1800. The first blood conditioning system may have a pump 1840 in the form of a peristaltic roller pump, a centrifugal blood pump or other suitable blood circulation pump. Preferably, the cerebral loop of the circulatory support system will also include a venous blood reservoir 1841, heat exchanger 1842 and blood oxygenator 1843 and in series with the first blood circulation pump 1840. Optionally, vacuum assist may be used to enhance venous drainage through the first venous drainage lumen 1888 of the superior vena cava catheter 1900.

Venous blood from the head and upper extremities enters the patient's superior vena cava and is drained out through the first venous drainage lumen 1888 of the venous drainage catheter 1900 as the first occlusion balloon 1896 prevents blood from traveling into the right atrium from the superior vena cava. The blood is oxygenated, cooled or warmed and recirculated by the first blood conditioning system 1847 to the head and upper extremities through the arch perfusion lumen 1805 of the arterial cannula 1800.

The corporeal loop of the circulatory support system is created by having venous drainage port(s) 1873 in fluid communication with inferior vena cava drainage lumen 1889. Attached to the second venous drainage lumen 1889 is a fitting having a barb connector 1880 coupled to tubing 1877 in fluid communication with an inflow port 1851 of a second blood circulation system 1855. After the blood is conditioned it is pumped through outflow port 1857 in fluid communication with tubing 1859 which is coupled to a barb connector 1812 in fluid communication the corporeal lumen 1808 of the aortic catheter 1800. The second blood circulation pump 1852 may be a peristaltic roller pump, a centrifugal blood pump or other suitable blood circulation pump. Preferably, the corporeal loop of the circulatory support system will also include a venous blood reservoir 1856, a blood oxygenator 1854 and heat exchanger 1853 in series with the second blood circulation pump 1852. Optionally, vacuum assist may be used to enhance venous drainage. Venous blood from the viscera and lower extremities enters the patient's inferior vena cava and is drained out through the second venous drainage lumen 1889 of the inferior vena cava catheter 1901. The blood is oxygenated, cooled or warmed and recirculated by the second blood circulation system 1855 to the viscera and lower extremities through the corporeal perfusion lumen 1808 of the arterial catheter 1800.

Optionally, the venous drainage catheters 1900 and 1901 may be made without occlusion balloons or alternatively, only one venous drainage catheter may have an occlusion balloon since isolation of the patient's right atrium and the coronary sinus is unnecessary. Furthermore, separate right atrium drainage port(s) 1882 can drain into either the superior vena cava catheter 1900 or the inferior vena cava catheter 1901 through a separate right atrium drainage lumen or alternatively combined into either the first 1898 or second 1889 drainage lumens of the superior 1900 and inferior 1901 vena cava catheters respectively. In this illustrative embodiment right atrium drainage port(s) are located on the catheter shaft 1166 of the inferior vena cava drainage catheter 1901.

As another alternative, the coronary circulation can be isolated by using a separate coronary sinus catheter 1850 for retrograde or antegrade administration of cardioplegia into the coronary arteries with complete isolation of the myocardium. A separate coronary perfusion loop can be created by connecting the coronary sinus lumen 1833 to the inflow of a third blood circulation pump 1835 and connecting the outflow of the pump to the cardioplegia lumen 1811 of the arterial cannula 1800. The third blood circulation pump 1831 may be a peristaltic roller pump, a centrifugal blood pump or other suitable blood circulation pump. Preferably, the coronary loop also includes a blood reservoir 1838 a cardioplegia source 1839, a blood oxygenator 1836 and heat exchanger 1837 in series with the third blood circulation pump 1831.

Alternatively, by eliminating the occlusion balloons 1897 or 1896, the patient's right atrium could be drained as part of the cerebral loop or the corporeal loop. For example, the superior vena cava catheter 1888 without an occlusion balloon or with the balloon deflated could be inserted into the superior vena cava and into the right atrium via the jugular vein or femoral vein. A coronary sinus catheter is inserted collaterally within the superior vena cava via the jugular vein or femoral vein to isolate the coronary circulation on the venous side and for antegrade or retrograde flow of blood, cardioplegia or other fluids. Suitable coronary sinus catheters for retrograde administration of cardioplegia can be found in U.S. Pat. Nos. 5,738,652; 5,722,963; 5,720,726; 5,662,607; 5,653,690; 5,643,231; 5,620,418; 5,617,854; 5,597,377; 5,558,644; 5,549,581; 5,533,957; 5,505,698; 5,488,960; 5,487,730; 5,466,216; 5,423,772; 5,423,745; 5,401,244; 5,395,331; 5,385,548; 5,385,540; 5,324,260; 5,197,952; 5,024,668; 5,021,045; 4,943,277; 4,927,412; 4,753,637; 4,648,384; 4,459,977, which are hereby incorporated by reference in their entirety.

When suction is necessary or desirable, a suction switch 1700 is activated stopping cardioplegia delivery by occluding tubing 1702 and opening tubing 1703 allowing suction source 1701 to withdraw fluid from the aortic root through distal opening 1816.

Figure 26A:
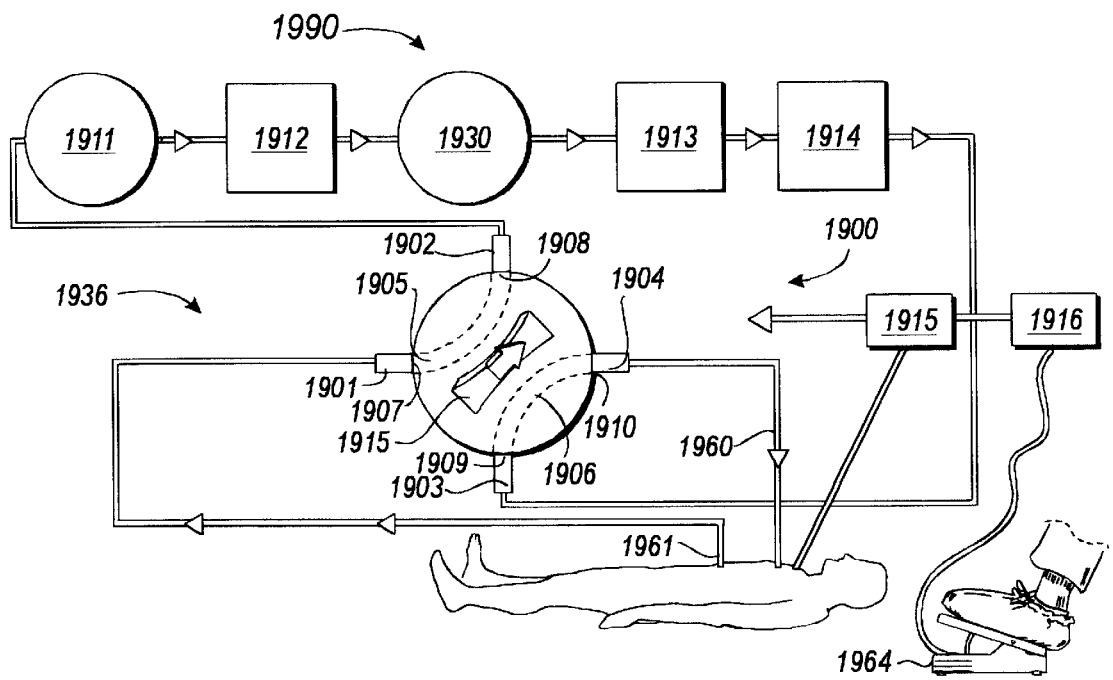
FIG. 26A is a schematic diagram illustrating an antegrade/retrograde switching mechanism positioned to provide antegrade flow.
Figure 26B:
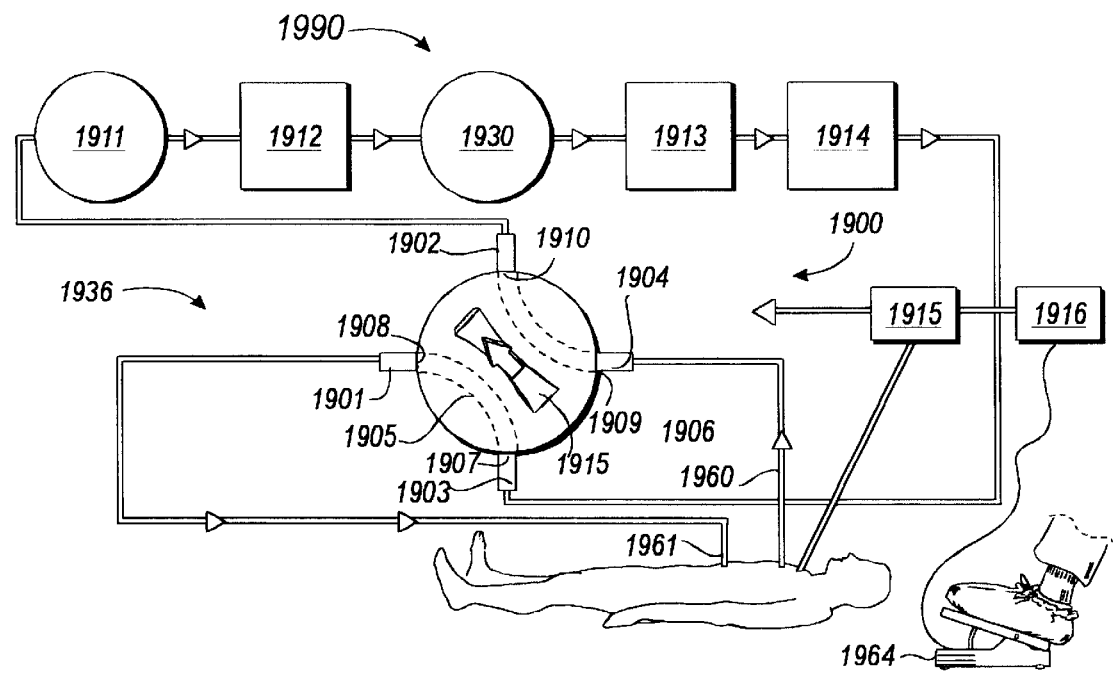
FIG. 26B is a schematic diagram illustrating an antegrade/retrograde switching mechanism positioned to provide retrograde flow.

FIGS. 26A and 26B illustrate a switch system configured for alternating between antegrade and retrograde flow. The switch system of the present invention may be activated by any number of methods including but not limited to pneumatic, emboli driven signals sent to a solenoid, manual activation, hydraulic, pneumatic mechanical, electronic, or computer means. One method of activating the switch system of the present invention is by using embolic sensing means 1915, for example, ultrasonography, which is configured to receive signals which are correlative to an embolic event. The signal is transmitted to the switch 1900, thereby activating retrograde or antegrade flow to the brain though the switching system 1936. Furthermore, the signal may also be displayed on a monitor 1916 so the clinician can record by computer means or by hand when embolic events have occurred. In addition the monitor 1916 may also be used to display oxygen saturation, temperature, pressure and other critical data during the procedure and may also be equipped with sound to indicate that an embolic event has occurred and the switch signal is being sent.

According to another method the switch system may be operated manually by adjusting the switch/valve assembly 1900 through a manual knob 1915. FIG. 26A illustrates the switch system of the present invention positioned in the antegrade position. FIG. 27B illustrates the switch system of the present invention after activation and the switch is now directing flow in the retrograde direction.

When the switch system is positioned in the antegrade position, venous fluid is withdrawn through a venous cannula/catheter 1961 and directed to the first communication channel 1905 of the valve assembly. The first communication channel 1905 has a first opening 1907 and a second opening 1908. In the antegrade position, the first opening 1907 of the first fluid communication channel 1905 opens to port 1901 and the second opening 1908 of the first communication channel 1905 opens to port 1902. The fluid is then conditioned in the CPB system 1990 and pumped through the second communication channel 1906 to arterial catheter/cannula 1960. The second fluid communication channel 1906 has a first opening 1909 and a second opening 1910 and, when in the antegrade position, the first opening 1909 opens to port 1901 and the second opening 1910 of the second fluid communication channel 1906 opens to port 1904. The CPB system 1990 preferably has a venous reservoir 1912, a peristaltic or roller pump 1930, and an integral heat exchanger 1913 membrane oxygenator 1914. Alternatively, vacuum assist 1911 or wall suction may be used to help drain fluid. Fluid is pumped into venous reservoir 1912 and is thereafter conditioned to the appropriate temperature and chemical composition through the heat exchanger 1913 and oxygenator 1914.

Illustrated in FIG. 26B is the switch system 1936 of the present invention configured for antegrade and retrograde fluid flow where the switch is placed in the retrograde position. The valve assembly 1900 is rotated counterclockwise, until the first opening 1909 of the second fluid communication channel 1906 is placed in fluid communication with port 1904 and the second opening 1910 of the second fluid communication channel 1906 is in fluid communication with port 1902. The first opening 1907 of the first fluid communication channel 1905 is placed in fluid communication with port 1901 and the second opening 1908 of the first communication channel 1905 is placed in fluid communication with port 1903. The valve serves as a switch, having a first position and a second position which enables the effective reverse of fluid flow to the patient's anatomy while still maintaining fluid flow to the CPB system in the same direction. The arterial cannula 1960 withdraws fluid with or without vacuum assist 1911 into the venous reservoir 1912 and is thereafter conditioned through the heat exchanger 1913 and oxygenator 1914. The fluid is pumped to the venous cannula 1961 where the patient's cerebral circulation is perfused in the retrograde direction.

Figure 27:
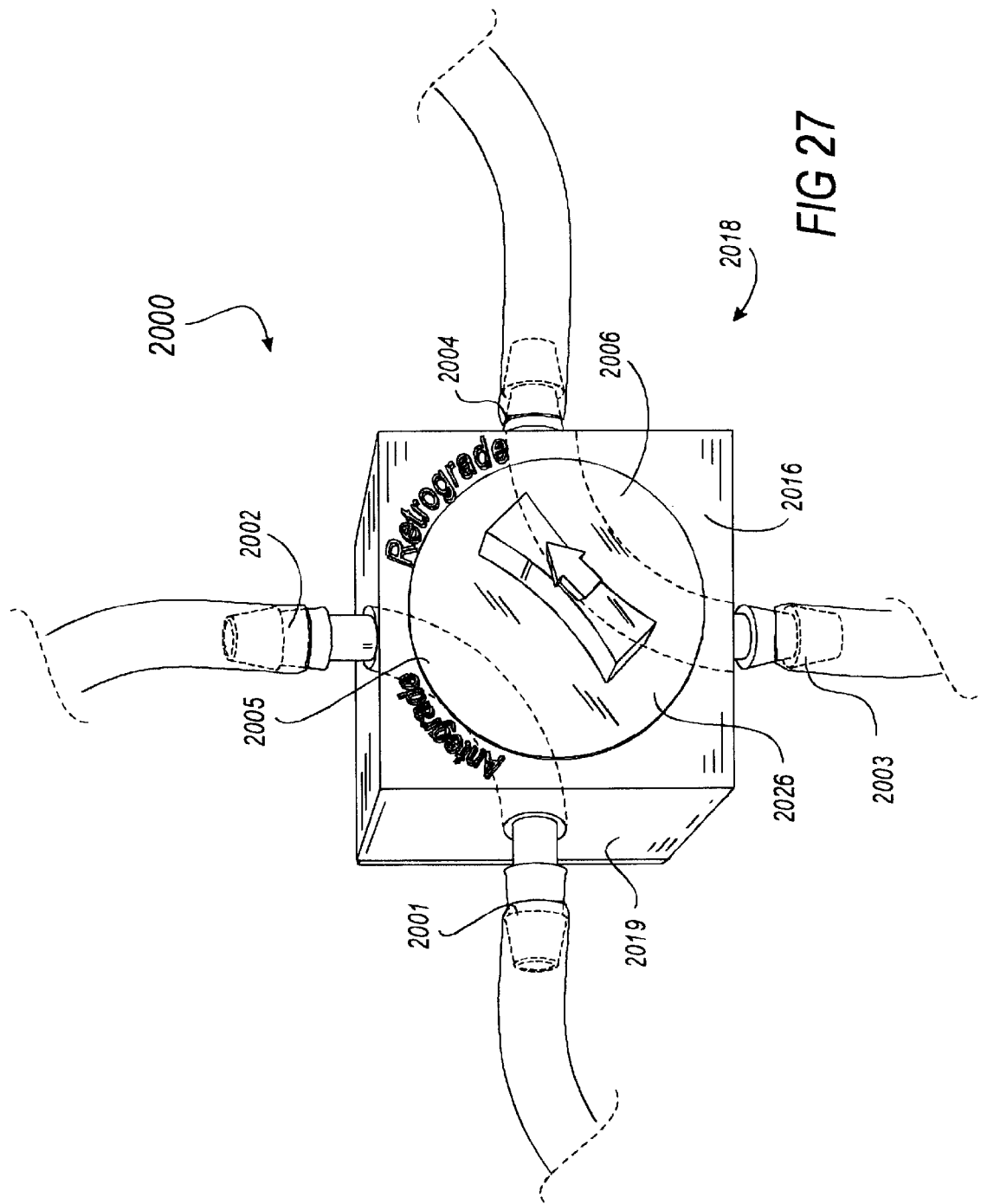
FIG. 27 is a perspective view of an assembled valve assembly.

FIG. 27 illustrates a perspective view of an assembled valve assembly 2000. The valve assembly 2000 is comprised of housing 2018, having a base 2019 and an insert 2026. In a preferred embodiment the housing 2018 is constructed of transparent materials so the clinician can visually see the flow of fluid through the fluid communication channels 2005 and 2006. The housing 2018 may be made of materials including but not limited to; polysulfane, polycarbonate, polystyrene, PEEK, nylon, PMMA, acetal, acrylic. Alternatively, if a clear housing 2018 is not desired stainless steel, or other metals may be used. Furthermore the housing 2018 may be injected molded, machined or cast.

Referring to FIGS. 27, 28A and 28B the base 2019 has ports 2001, 2002, 2003 and 2004, in the form of barb connectors, or other suitable fittings which are sized and configured to be coupled to tubing, for communication of fluid between a venous cannula, an arterial cannula and a CPB machine. Furthermore, the base has a cutout or cavity 2098, which is sized and dimensioned for receiving the rotatable insert 2026. The base 2019 has an arcuate shaped slot 2034 that is sized and dimensioned for the slidable movement of the rotation limiter 2027 within the slot 2034. Alternatively, the insert 2026 could be manufactured to have the slot 2034 and the limiter 2027 as part of the base.

Referring more specifically to FIGS. 28A and 28B the insert 2026 has a top surface 2085 and a bottom surface 2084 and has the shape of a cylinder. The bottom surface 2084 of the insert 2026 has a rotation limiter 2027 that extends from the bottom surface 2084 of the insert 2026. The rotation limiter 2027 allows the insert to be rotated 90 degrees in the clockwise or counterclockwise direction. The rotation limiter 2027 may be attached to the insert 2026 or alternatively may be designed as an integral component of the mold of the insert 2026. The bottom surface 2084 should also have a smooth surface to limit frictional resistance with the base 2019. The insert 2026 is slightly larger than the base 2019 and is compressible within the cutout 2098 and has a low frictional surface so when it is placed inside the base 2019 a mechanical seal is created. Alternatively, a gasket with 4 cutouts aligned with the 4 ports may be used to create a fluid seal between the insert and the base or alternatively 4 separate gaskets or O-rings may be used for each port. The insert 2026 has a first communication channel 2005 and a second communication channel 2006 creating two separate fluid channels for the communication of fluid. In this illustrative embodiment, the fluid channels 2005 and 2006 are arcuate in shape. Alternatively the channels may be straight or any other arrangement which facilitates the ability for rotational alternating communication. The first communication channel 2005 has a first opening 2007 and a second opening 2008. The second communication channel 2006 has a first opening 2009 and a second opening 2010. The insert 2026 may be made of any number of materials including but not limited to, polysulfane, polycarbonate, polystyrene, PEEK, nylon, PMMA, acetal, acrylic and is rotatable within the base 2019 in a clockwise and counterclockwise rotation.

In addition to being transparent or opaque, the base has written directional instructions indicating how the valve assembly is currently positioned.

A knob 2015 may be coupled directly to the insert 2026 through a connecting rod or adhesives. Alternatively, in electronic or computer activated embodiments no handle may be used since the insert 2026 will be rotated through electronic and mechanical interaction. Alternatively, the switch/valve could also be implemented as a spool valve or a series of separate solenoid valves to accomplish the same function as the switch/valve 2000.

What is claimed is:

1. An aortic catheter comprising:
    a catheter shaft having an outer tubular member and an inner tubular member, said inner tubular member slidably disposed within said outer tubular member;
    an occlusion member expandable from said catheter shaft;
    an arch lumen defined by an annular space between said inner and outer tubular members extending at lest in part along the length of said catheter shaft and having at least one distal arch opening, a proximal arch lumen connector in fluid communication with said arch lumen and configured for connection to a CPB machine;
    a corporeal lumen having at least one distal corporeal opening positioned distal to said occlusion member, a proximal corporeal lumen connector in fluid communication with said corporeal lumen and configured for connection to a CPB machine; and
    a suction source in communication with a port in the catheter shaft proximal to said occlusion device.

2. The aortic catheter of claim 1, wherein said at least one distal arch opening is further comprised of one or more distal arch perfusion ports.

3. The aortic catheter of claim 1, wherein said at least one distal corporeal opening is further comprised of one or more distal corporeal perfusion ports.

4. The aortic catheter of claim 1, further comprising an actuating lumen having a proximal opening coupled to an actuating source and a distal opening configured to expand said occlusion member.

5. The aortic catheter of claim 1, wherein said occlusion member is a balloon.

6. The aortic catheter of claim 1, wherein said arch lumen is sized and configured to perfuse fluid at a first temperature, flow rate and chemical composition to the cerebral subcirculation.

7. The aortic catheter of claim 1, wherein said corporeal lumen is sized and configured to perfuse blood at a second temperature, flow rate and chemical composition to the corporeal subcirculation.

8. The aortic catheter of claim 1, wherein said occlusion member is positioned on said outer tubular member.

9. The aortic catheter of claim 1, further comprising a second occlusion member.

10. The aortic catheter of claim 9, wherein said second occlusion member is mounted on said inner tubular member.

11. The aortic catheter of claim 9, wherein said second occlusion member is eccentric.

12. The aortic catheter of claim 1, wherein said catheter shaft is coated with a lubricious material.

13. The aortic catheter of claim 1, wherein said catheter shaft is coated with medicated material.

14. The aortic catheter of claim 1, wherein said catheter shaft is coated with echogenic material.

15. The aortic catheter of claim 1, wherein said inner tubular member is coil reinforced.

16. A system for perfusing a patient's aorta comprising:
    a CPB machine;
    an aortic catheter comprising:
        a catheter shaft having an outer tubular member and an inner tubular member configured in a coaxial relationship such that an annular space is created therebetween;
        said outer tubular member and said inner tubular member moveable relative to one another;
        an occlusion member expandable from said catheter shaft;
        an arch lumen defined by said annular space extending at least in part along the length of said catheter shaft and having at least one distal arch opening, a proximal arch lumen connector in fluid communication with said arch lumen and connected to the CPB machine;
        a corporeal lumen defined by the internal diameter of said inner tubular member having at least one distal corporeal opening located distal to said occlusion member, a proximal corporeal lumen connector in fluid communication with said corporeal lumen and connected to the CPB machine;
        a suction source in communication with a port in the catheter shaft proximal to said occlusion device; and
        a venous cannula having an inflow port configured for receiving deoxygenated blood, and a proximal end residing outside the patent configured for communicating said deoxygenated blood to said CPB machine.

17. The system for perfusing a patient's aorta of claim 16, further comprising a switch having a first position and a second position and configured for alternating the communication of said arch lumen from said suction source to said oxygenating means.

18. The system for perfusing a patient's aorta of claim 16, wherein said occlusion member is a balloon in fluid communication with an actuating lumen for expanding said balloon.

19. The system for perfusing a patient's aorta of claim 16, wherein said arch lumen is sized and configured to perfuse fluid at a predetermined temperature, flow rate and chemical composition to the cerebral subcirculation.

20. The system for perfusing a patient's aorta of claim 16, wherein said corporeal lumen is sized and configured to perfuse blood at a predetermined temperature, flow rate and chemical composition to the corporeal subcirculation.

21. The system for perfusing a patient's aorta of claim 16, further comprising a second occlusion member.

22. The system for perfusing a patient's aorta of claim 16, wherein said second occlusion member is mounted on said outer tubular member.

* * * * *